(12) United States Patent
Devitt et al.

(10) Patent No.: US 10,967,343 B2
(45) Date of Patent: Apr. 6, 2021

(54) SPRAY CONFIGURATIONS FOR DUAL CHAMBER MIXING DEVICES

(71) Applicant: UNL Holdings LLC, New York, NY (US)

(72) Inventors: Shaun R. Devitt, Wayne, PA (US); Jon Suh, Blue Bell, PA (US)

(73) Assignee: UNL HOLDINGS LLC, New York, NY (US)

( * ) Notice: Subject to any disclaimer, the term of this patent is extended or adjusted under 35 U.S.C. 154(b) by 400 days.

(21) Appl. No.: 15/114,697

(22) PCT Filed: Jan. 30, 2015

(86) PCT No.: PCT/US2015/013791
§ 371 (c)(1),
(2) Date: Jul. 27, 2016

(87) PCT Pub. No.: WO2015/116941
PCT Pub. Date: Aug. 6, 2015

(65) Prior Publication Data
US 2016/0346747 A1    Dec. 1, 2016

Related U.S. Application Data

(60) Provisional application No. 61/933,502, filed on Jan. 30, 2014.

(51) Int. Cl.
*B01F 13/00* (2006.01)
*A61M 5/28* (2006.01)
(Continued)

(52) U.S. Cl.
CPC .......... *B01F 13/0023* (2013.01); *A61M 5/19* (2013.01); *A61M 5/284* (2013.01); *B01F 5/0082* (2013.01);
(Continued)

(58) Field of Classification Search
CPC B05B 1/14; B05B 7/065; B05B 7/066; B05B 7/0876; B01J 19/26; B01F 5/0082;
(Continued)

(56) References Cited

U.S. PATENT DOCUMENTS 3,410,250 A    11/1968  Kulie et al.
4,183,897 A  *  1/1980  Lanteri .................... B01J 10/02
                                                        261/112.1
(Continued)

OTHER PUBLICATIONS

European Patent Office, International Search Report in International Patent Application No. PCT/US2015/013791. dated Apr. 23, 2015, 3 pp.
(Continued)

*Primary Examiner* — Tony G Soohoo
(74) *Attorney, Agent, or Firm* — Hamilton, Brook, Smith & Reynolds, P.C.

(57) ABSTRACT

A treatment apparatus for a mixing device having a concentric barrel configuration. The treatment apparatus includes a manifold including an input end and an output end. The treatment apparatus also includes a conduit body having a manifold end and a nozzle end. The manifold end is connected to the output end of the manifold, and the conduit body includes at least one nozzle at the nozzle end of the conduit body opposite the manifold. At least one fluid pathway is formed between the input end of the manifold, the conduit body, and the at least one nozzle.

16 Claims, 18 Drawing Sheets

(51) Int. Cl.
*A61M 5/19* (2006.01)
*B05B 1/14* (2006.01)
*B05B 7/08* (2006.01)
*B01F 5/00* (2006.01)
*B01F 15/02* (2006.01)
*B01F 5/04* (2006.01)
*A61M 5/31* (2006.01)
*B01F 15/00* (2006.01)

(52) U.S. Cl.
CPC ............ *B01F 5/048* (2013.01); *B01F 5/0471* (2013.01); *B01F 5/0475* (2013.01); *B01F 15/0223* (2013.01); *B01F 15/0237* (2013.01); *B05B 1/14* (2013.01); *B05B 7/0876* (2013.01); *A61M 2005/3131* (2013.01); *A61M 2205/0222* (2013.01); *A61M 2205/0238* (2013.01); *A61M 2207/10* (2013.01); *B01F 2015/00116* (2013.01)

(58) Field of Classification Search
CPC .... B01F 5/0405; B01F 5/0453; B01F 5/0493; B01F 5/0456; B01F 5/048; B01F 5/0475; B01F 5/0471; B01F 13/0023; B01F 15/0223; B01F 2015/00116; B01F 15/0237; A61M 5/19; A61M 5/284; A61M 2205/0222; A61M 2005/3131; A61M 2207/10; A61M 2205/0238

USPC ............................ 366/178.2, 181.6, 131, 134
See application file for complete search history.

(56) References Cited

U.S. PATENT DOCUMENTS

| | | | |
|---|---|---|---|
| 2009/0031923 A1* | 2/2009 | Teshima | B01F 5/0453 106/400 |
| 2009/0251989 A1* | 10/2009 | Pfefferle | B01F 5/0453 366/340 |
| 2010/0204495 A1* | 8/2010 | Andresen | B01F 3/04049 549/523 |
| 2011/0088617 A1* | 4/2011 | Bottger | B05B 7/0416 118/317 |
| 2012/0325854 A1* | 12/2012 | Ashmead | B01F 5/0077 222/143 |
| 2013/0283756 A1 | 10/2013 | Baker et al. | |
| 2013/0343147 A1* | 12/2013 | Heinesen | B01F 3/02 366/107 |

OTHER PUBLICATIONS

European Patent Office, Written Opinion in International Patent Application No. PCT/US2015/013791. dated Apr. 23, 2015, 5 pp.

* cited by examiner

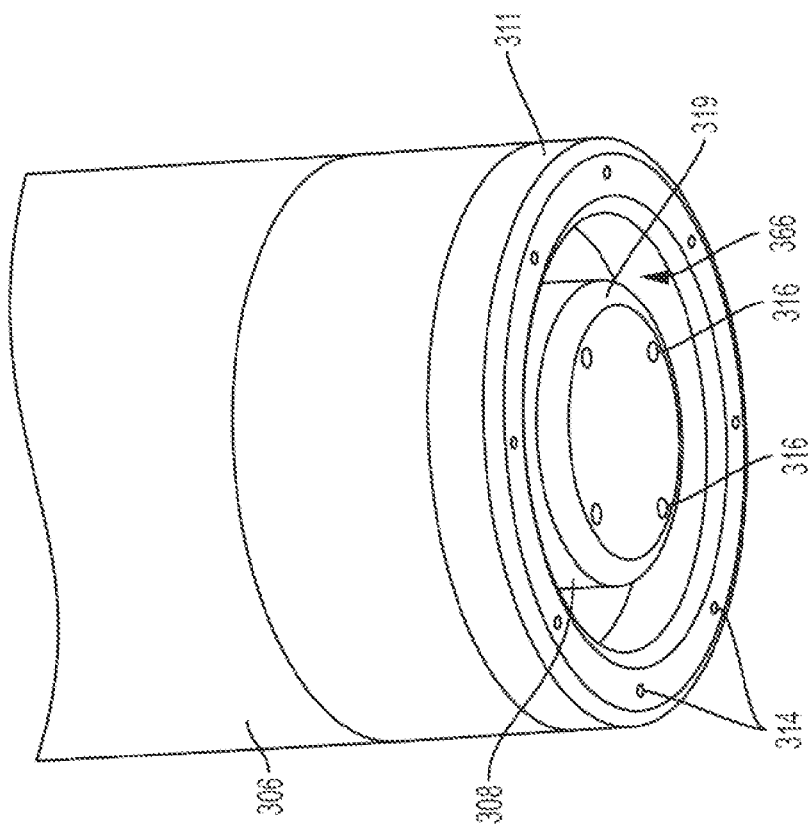
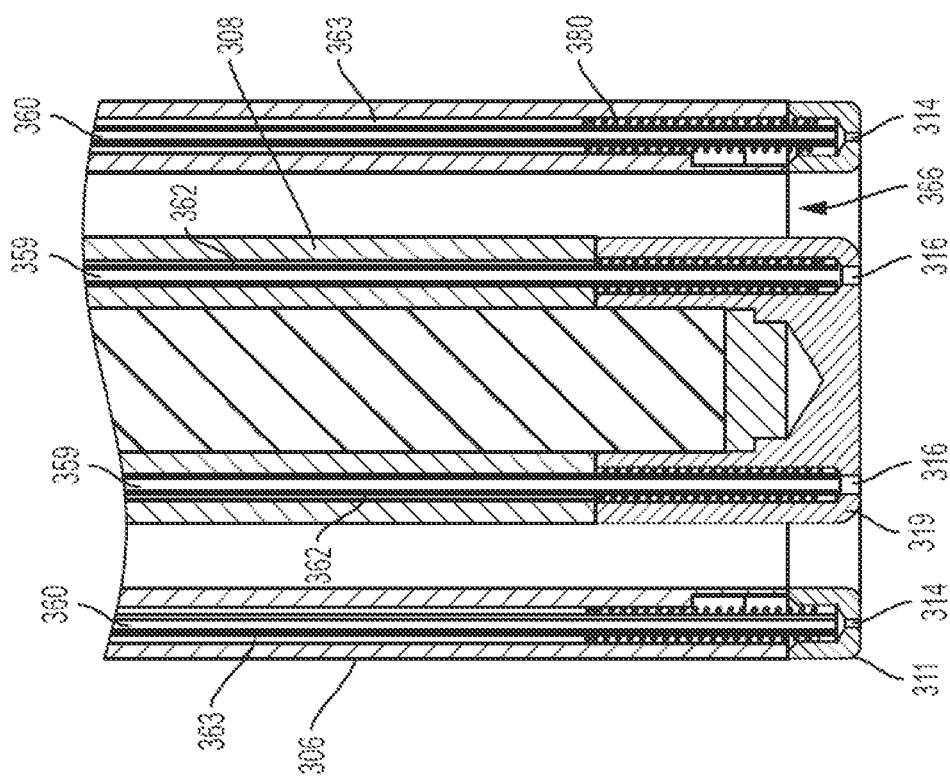

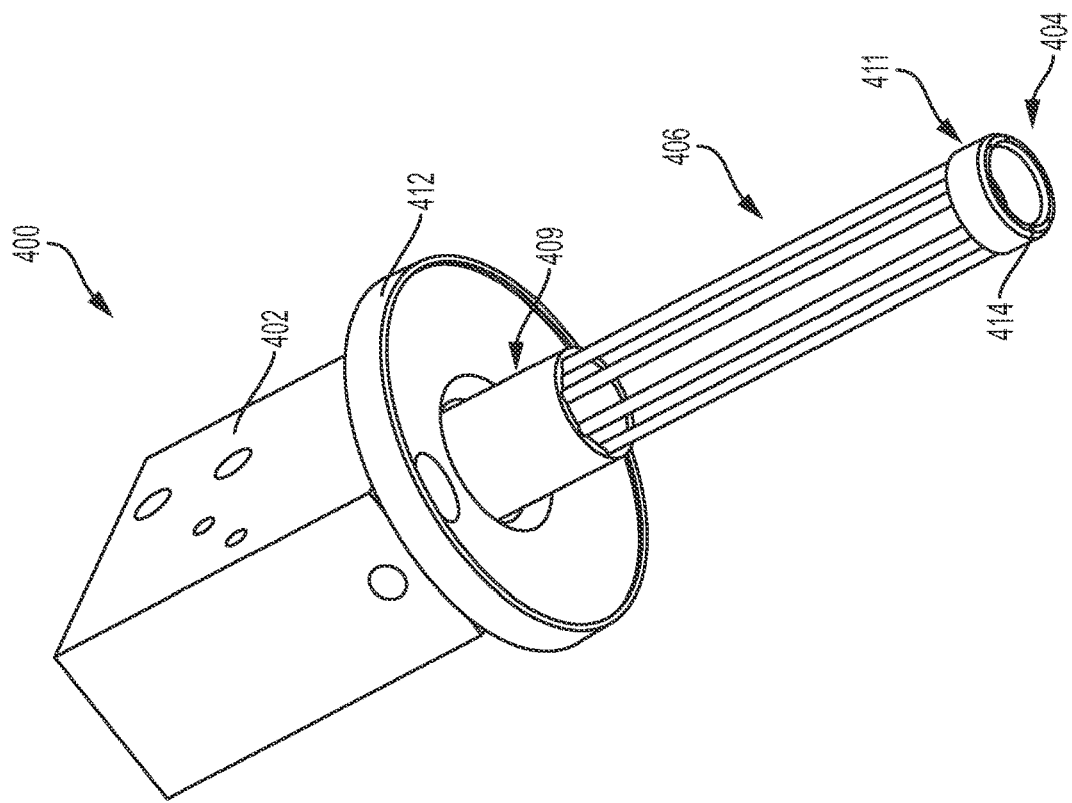
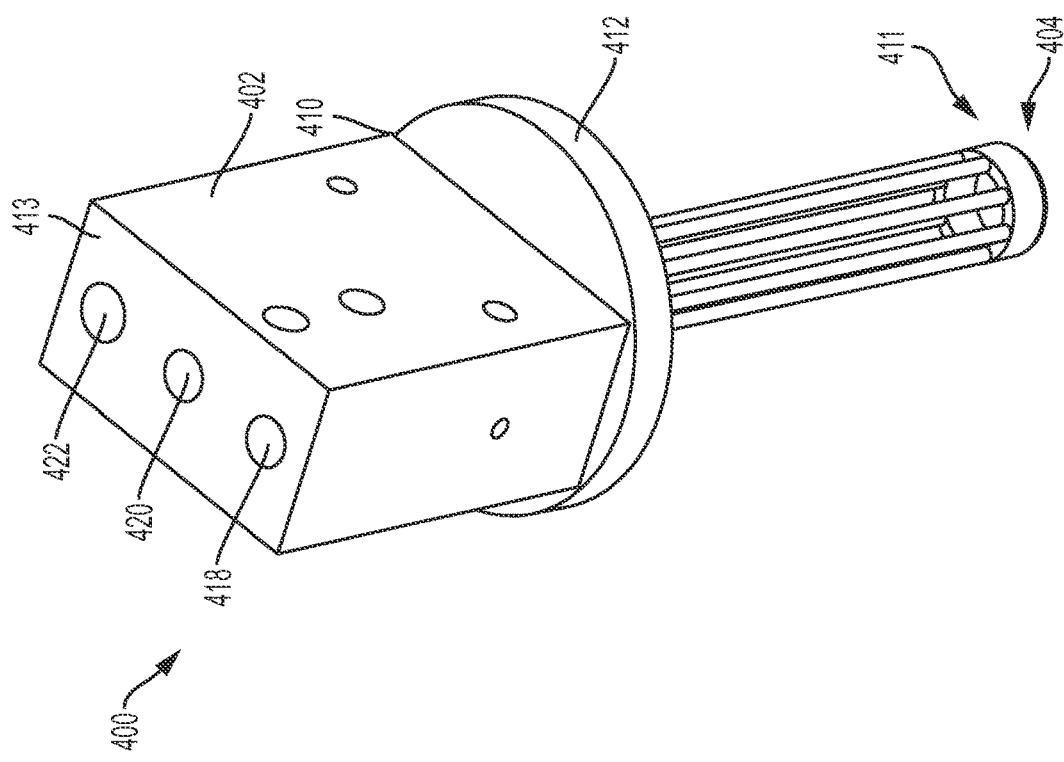

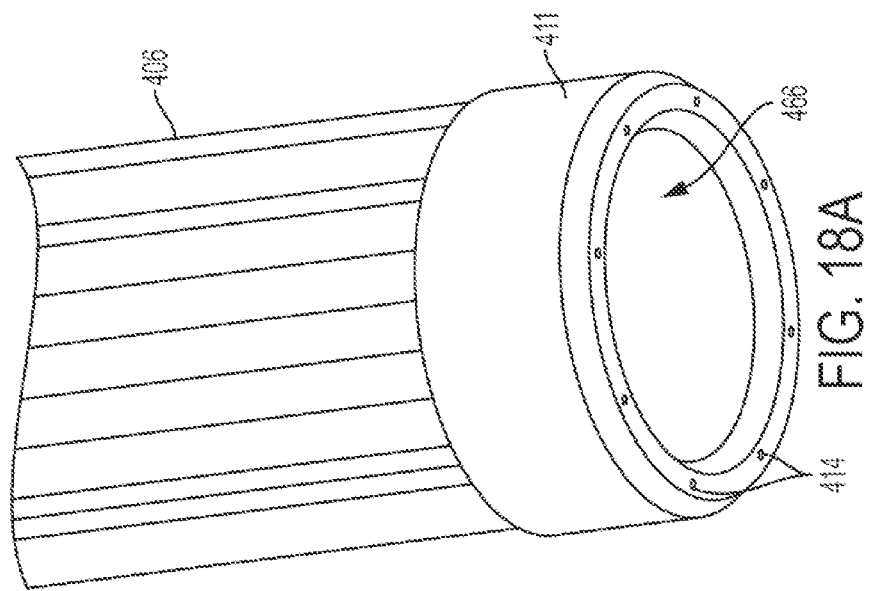
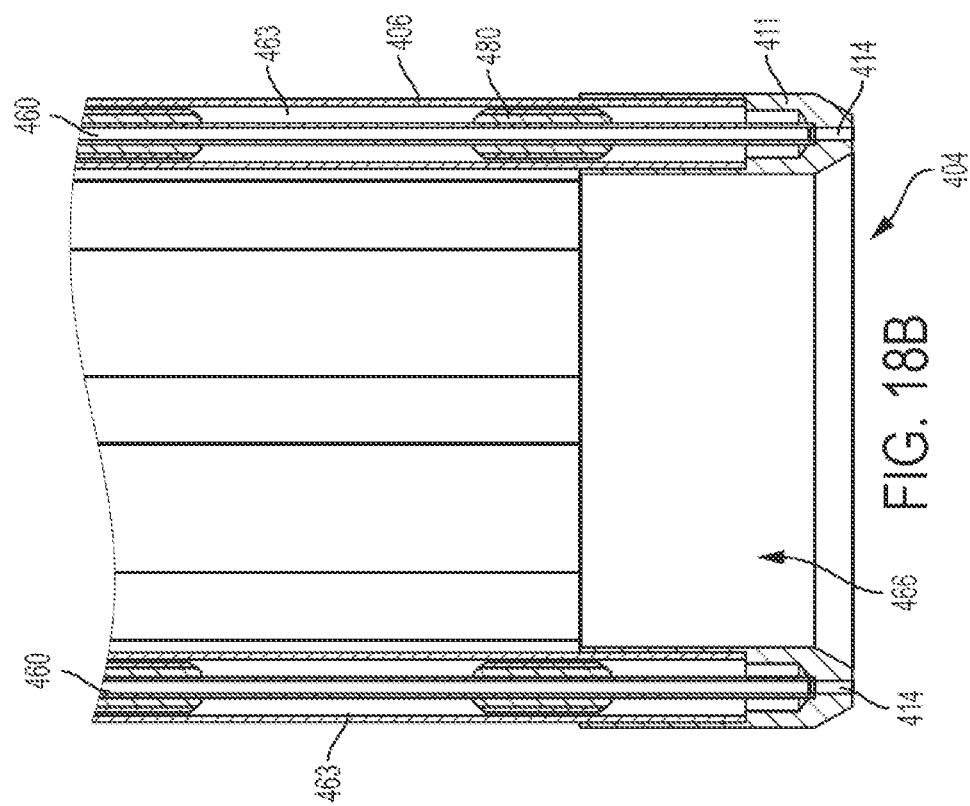

SPRAY CONFIGURATIONS FOR DUAL CHAMBER MIXING DEVICES

CROSS-REFERENCE TO RELATED APPLICATIONS

This patent application is national phase application of International Patent Application No. PCT/US2015/013791, filed Jan. 30, 2015, which claims benefit of U.S. Provisional Patent Application No. 61/933,502, filed Jan. 30, 2014, both of which are incorporated by reference herein in their entireties for purposes.

FIELD

THIS INVENTION relates to mixing devices. More particularly, this invention relates to spray configurations for mixing devices, such as mixing syringes, useful to apply silicone or lubricant to the mixing device to improve their functionality. The resulting siliconized or coated mixing devices are capable of storage, mixing, and injection of one or more pharmaceutical substances.

BACKGROUND

It is known to provide syringes that comprise a mixing device for mixing deliverable substances prior to injection. This allows, for example, a diluent to be added to a dehydrated, lyophilized, desiccated or powdered active substance immediately prior to injection, which is particularly useful for substances that are subject to degradation or loss of activity when stored in a hydrated form.

The majority of mixing devices for syringes utilize sequential chambers, wherein the syringe has one barrel having a first proximal chamber and a second distal chamber separated by, for example, a membrane or elastomeric seal. A number of such sequential-chamber mixing syringes utilize a bypass protrusion at a section of the barrel to enable fluid in the proximal chamber to bypass the dividing membrane and mix with the fluid or powder in the distal chamber.

However, some mixing syringes utilize concentric barrel configurations. The concentric barrel mixing syringes to date, however, require complex assemblies, multiple operation steps by the user, or other particular nuances that make them difficult to manufacture, assemble, or operate. For examples, some existing concentric barrel mixing syringes require concentric inner and outer barrels that are selectively rotatable with respect to each other, and require one or more sealing rings which contain a passage means therein. The barrels must be rotated to align a hole in the inner barrel with the passage means in a sealing ring. The passage means in the sealing ring includes a radially extending opening through the sealing ring and a groove extending longitudinally of the sealing ring from the radially extending opening. This arrangement being such that the groove connects the outer barrel with the radially extending opening and the radially extending opening selectively connects the groove with the hole in the inner barrel. This enables flow of fluid from the outer barrel into to the inner barrel to thereby mix the fluid with a substance in the inner barrel. Such configurations require complex components and cumbersome requirements for the user to operate the device.

Other concentric barrel designs utilize outer and inner telescopic tubular elements seated inside a barrel and coaxial with the longitudinal axis. The outer tubular element and barrel form a chamber which holds a reservoir of liquid. The outer tubular element has a fluid passageway therein that allows the liquid to flow from the chamber into the inner tubular element. The inner tubular element has an end nearby the injection port with a seal thereon that has an orifice therein. This inner tubular element receives the end of the plunger with the resilient seal thereon. Accordingly, such mixing syringe configurations require three tubular elements, with the outer and inner concentric chambers residing inside a third barrel.

There are numerous complexities associated with the use of concentric barrels for mixing syringe configurations. In addition to those described above, mixing syringes utilizing concentric barrels must also address factors such as maintenance of container sterility, interaction of components for sealing, venting requirements, and distribution of internal forces, among others. Some dual chambered syringes have concentric inner and outer barrels that form an annular space to hold a fluid and utilize one or more apertures between the inner and outer barrels to enable flow of a liquid from the annular space into the inner barrel and thereby mix the liquid with a substance in the inner barrel. The liquid is forced from the annular into the inner barrel by depression of a plunger slidably movable in the annular space. First and second sealing bands are slidably received about the inner barrel in the annular space and are mutually spaced therealong. The position of the sealing bands can dictate how sterility of the fluid path is maintained, how internal forces are distributed, and how venting occurs. For example, both of the sealing bands may be initially positioned above the aperture to form a sealed annular volume for the first liquid component. Because of this arrangement, the aperture also must act as a vent to enable any air in the annular space distal to the second sealing band, which space must be sterilized, to be expelled via the aperture upon depression of the plunger. This venting requirement may cause difficulties and require additional equipment and processing steps, such as requiring filling the inner chamber under vacuum to remove all air from the inner chamber and the distal portion of the outer barrel below the second reconstitution seal.

Additionally, barrels, such as a syringes and vials are known to utilize siliconization or lubrication, for example, to improve their functionality. For example, siliconization of syringe barrels is known to improve the glide forces of the plunger as a user depresses it for drug delivery. Concentric barrel designs may similarly utilize siliconization or lubrication, but are not readily capable of being prepared in standard assemblies or by known application methods, especially for the annular space between barrels.

SUMMARY

The present invention provides a treatment system having a treatment apparatus, a fluid conduit, and a nozzle to treat a mixing device having a concentric barrel configuration. A single nozzle configuration or a multi-nozzle configuration may be utilized within the scope of the present embodiments. The nozzles may be fixed in position or rotatable/translatable within the mixing device, and/or the system may be configured to permit and utilize the rotation/translation of the mixing device to treat the desired surfaces. Additionally or alternatively, the mixing device may be treated by a system that includes one or more of: washing, masking, treating, and assembling, such as by glue or adhesive, the components of the mixing device.

In an embodiment, the present disclosure describes a treatment apparatus for a mixing device having a concentric barrel configuration. The treatment apparatus comprises a manifold including an input end and an output end. The treatment apparatus also comprises a conduit body having a manifold end and a nozzle end. The manifold end is connected to the output end of the manifold, and the conduit body includes at least one nozzle at the nozzle end of the conduit body opposite the manifold. At least one fluid pathway is formed between the input end of the manifold, the conduit body, and the at least one nozzle.

A treatment apparatus for a mixing device having a concentric barrel configuration. The treatment apparatus comprises a manifold including an input end and an output end. A first fluid bore and a second fluid bore are formed into the input end of the manifold. The treatment apparatus includes a substantially tubular outer conduit body having a manifold end and a nozzle end. The manifold end is connected to the output end of the manifold. The outer conduit body includes a plurality of outer nozzles disposed in an annular pattern at the nozzle end of the outer conduit body opposite the manifold. The outer conduit body also includes a plurality of outer fluid conduits disposed within the outer conduit body, each of the outer fluid conduits being in fluid communication with both the second fluid bore and one of the plurality of outer nozzles. The outer conduit body includes at least one outer conduit passage formed within the outer conduit body, each of the outer conduit passages being in fluid communication with both the first fluid bore and one of the plurality of outer nozzles. The first fluid bore and each of the plurality of outer conduit passages define at least a portion of a first fluid pathway formed between the input end of the manifold and one of the plurality of outer nozzles. The second fluid bore and each of the plurality of outer fluid conduits define at least a portion of a second fluid pathway formed between the input end of the manifold and one of the plurality of outer nozzles.

A method of treating a mixing device having an inner barrel and a concentric outer barrel. The method comprises providing at least one treatment apparatus. Each treatment apparatus comprises a manifold having an input end and an output end. A first fluid bore and a second fluid bore are formed into the input end of the manifold. The treatment apparatus also includes a conduit body with a manifold end connected to the output end of the manifold. The conduit body includes at least one nozzle at a nozzle end of the conduit body opposite the manifold end, at least one fluid conduit providing fluid communication between the second fluid bore and the at least one nozzle, and at least one conduit passage providing fluid communication between the first fluid bore and the at least one nozzle. The first fluid bore and the at least one conduit passage define a first fluid pathway formed between the input end of the manifold and the at least one nozzle. The second fluid bore and the at least one fluid conduit define a second fluid pathway formed between the input end of the manifold and the at least one nozzle. The method also includes feeding a first fluid into the first fluid bore such that the first fluid flows along the first fluid pathway and is expelled through the at least one nozzle. The method includes feeding a second fluid into the second fluid bore simultaneous to feeding the first fluid into the first fluid bore such that the second fluid flows along the second fluid pathway and is expelled through the at least one nozzle simultaneously with the first fluid. The method also includes disposing the at least one nozzle within at least one of the inner barrel or the outer barrel of the mixing device.

Throughout this specification, unless otherwise indicated, "comprise", "comprises" and "comprising" are used inclusively rather than exclusively, so that a stated integer or group of integers may include one or more other non-stated integers or groups of integers.

BRIEF DESCRIPTION OF THE DRAWINGS

Non-limiting embodiments of the invention are described herein with reference to the following drawings wherein:

FIG. 12A shows an enlarged, isometric view of a portion of the treatment apparatus of FIG. 5A.

FIG. 12B shows an enlarged, front sectional view a portion of the treatment apparatus of FIG. 5A;

FIG. 13A shows an isometric view of a treatment apparatus, according to another embodiment of the present invention, having an annular nozzle configuration;

FIG. 13B shows another isometric view of the treatment apparatus of FIG. 13A;

FIG. 18A shows an enlarged, isometric view of a portion of the treatment apparatus of FIG. 13A;

FIG. 18B shows an enlarged, front sectional view of a portion of the treatment apparatus of FIG. 13A;

DETAILED DESCRIPTION

Figures 1A, 1B:
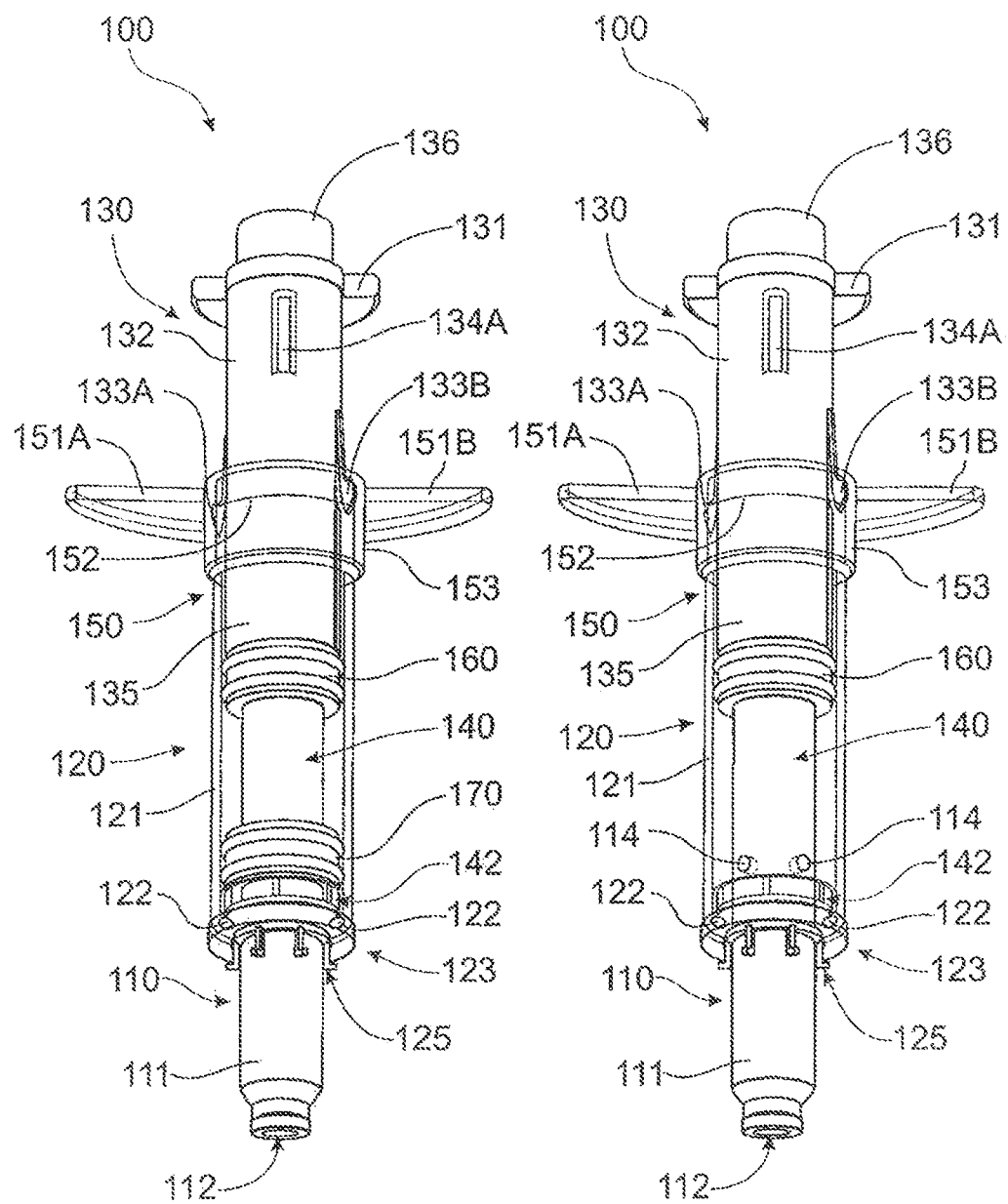
FIG. 1A shows a side view of an embodiment of a mixing device.
FIG. 1B shows a side view of an embodiment of a mixing device with distal seal removed to show fluid path apertures.

Suitably, the mixing device may be according to that which is described in International Publication WO2013/020170, which is incorporated by reference in its entirety for all purposes. Referring to FIG. 1A and FIG. 1B an embodiment of mixing device 100 comprises inner barrel 110 comprising wall 111 and inner chamber 112, outer barrel 120 comprising wall 121 and mixing plunger 130. Outer chamber 140 is formed between wall 111 of inner barrel 110 and wall 121 of outer barrel 120. Inner barrel 110 and outer barrel 120 may be made of any of a number of materials including plastics and glass, but are preferably made of glass Inner barrel 110 and outer barrel 120 are in a substantially concentric relationship, such that inner barrel 110 and outer barrel 120 possess a substantially common, central longitudinal axis. Inner barrel 110 and outer barrel 120 are non-rotatable with respect to each other.

Outer barrel extension 150 comprises finger grips 151A, B to assist gripping by a user. Outer barrel extension 150 may be integrally formed in outer barrel 120 or may be a separate component affixed to outer barrel 120. Outer barrel extension 150 further comprises inner lip 152 and locking ring 153, the functions of which will be described in more detail hereinafter.

Typically, outer chamber 140 contains a liquid substance and inner chamber 112 contains a solid substance, whereby the liquid substance is mixable with the solid substance in the inner chamber 112 to form a mixed substance suitable for injection. In at least one embodiment, however, the outer chamber 140 and inner chamber 112 both contain liquid substances.

In the embodiment shown in FIGS. 1A and 1B, outer barrel 120 is shorter than inner barrel 110. This configuration provides certain benefits such as, for example, allowing a heat transfer sleeve (not shown) to be placed around and in direct contact with a portion of inner barrel 110. This is useful to enable in situ lyophilization of a liquid substance located in inner chamber 112, by permitting filling with a liquid substance and then lyophilizing the liquid substance into a powder during or after manufacture of mixing device 100.

In other embodiments, inner barrel 110 and outer barrel 120 are of substantially similar length. This embodiment may be more aesthetically pleasing or provide additional volume by way of outer chamber 140. Also located in outer chamber 140 are first or proximal seal 160 and second or distal seal 170 slidably located therein.

Outer barrel 120 further comprises vent cap 123 comprising plurality of vents 122, whereby vented space 142 is located between vents 122 and second or distal seal 170. Because the substances do not contact this vented space 142, vented space 142 may be unsterile and open to the atmosphere. This feature enables displacement of second or distal seal 170 towards plurality of vents 122 during the mixing step of operation, thereby opening one or more apertures 114 for passage of fluid from the outer chamber to the inner chamber. The fluid path from outer chamber 140 to inner chamber 112 remains sterile as a result of the displaced location of second or distal seal 170.

Mixing plunger 130 comprises button 131 and cylindrical shaft 132 which is slidably, axially moveable within outer chamber 140. Mixing plunger 130 may further comprise spring prongs 133A, B located on shaft 132 biased outwardly from shaft 132. Spring prongs 133A, B are moved inwardly (i.e., against bias) when inserting mixing plunger 130 into outer chamber 140 of mixing device 100. In the assembled mixing device 100, spring prongs 133A, B prevent removal of mixing plunger 130 from outer chamber 140. Mixing plunger 130 further comprises locking prongs 134A, B (134B not visible) located on shaft 132 biased outwardly from shaft 132. Locking prongs 134A, B are biased outwardly to engage inner lip 152 of barrel extension 150 to facilitate locking mixing plunger 130 from proximal movement after mixing is complete.

Mixing plunger 130 further comprises release ring 136 at a proximal end (i.e., proximal to a user) of cylindrical shaft 132. Release ring 136 may be a separate component or an integral component of mixing plunger 130. In a preferred embodiment, release ring 136 is a smaller diameter proximal portion of mixing plunger 130. The functions of release ring 136 will be described in more detail hereinafter.

Figure 2:
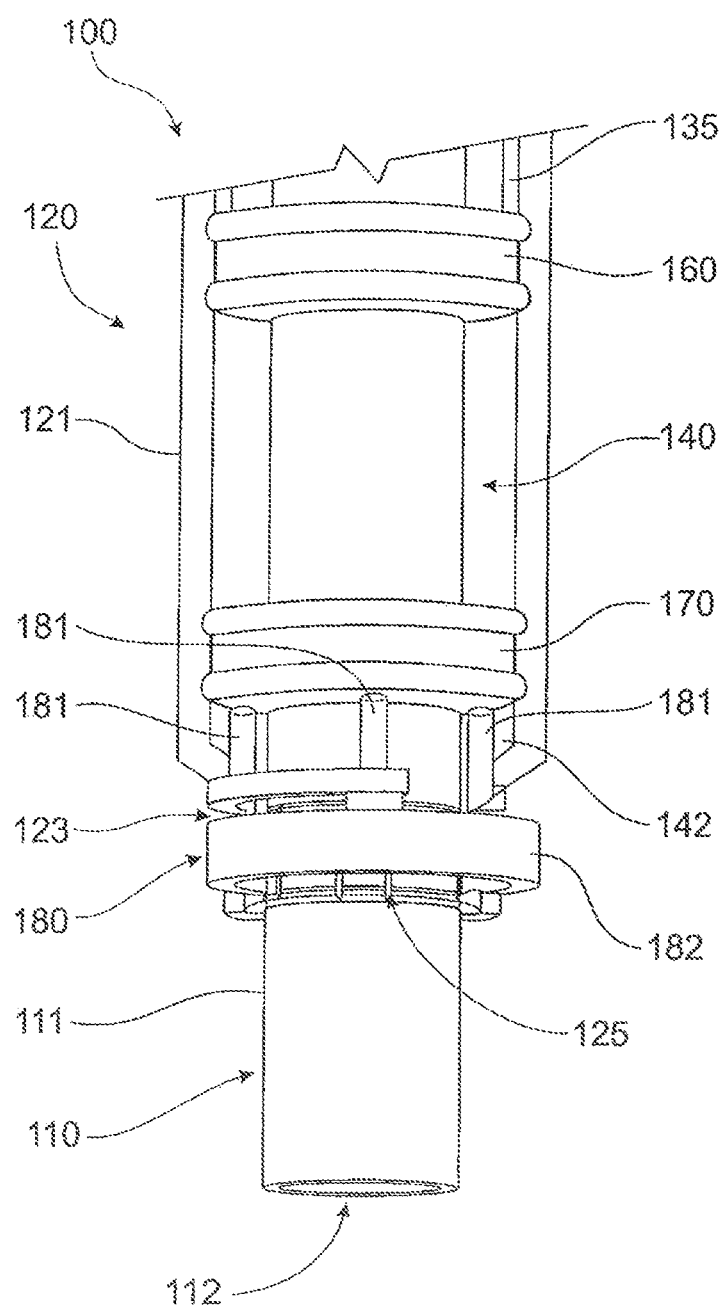
FIG. 2 shows an embodiment of a mixing device further comprising an optional safety cap mounted thereto.

First or proximal seal 160 is in contact with the distal end 135 of cylindrical shaft 132 of mixing plunger 130. Second or distal seal 170 is positioned distally from proximal seal 160 within outer chamber 140. First or proximal seal 160 is axially, slidably moveable within outer chamber 140 by contact with and movement of the shaft 132 of mixing plunger 130. As best seen in FIG. 1B, apertures 114 on inner barrel wall 111 provide a fluid path that allows fluid from outer chamber 140 to flow into inner chamber 112. Initially, second or distal seal 170 is in sealing engagement with apertures 114 (e.g., covering apertures 114; compare FIG. 1A and FIG. 1B). FIG. 2 shows an enlarged view of the mixing device described in International Publication WO2013/020170, to provide better context of the aspects of the device which may be siliconized, lubricated, or otherwise treated by the embodiments of the present invention.

Figure 3:
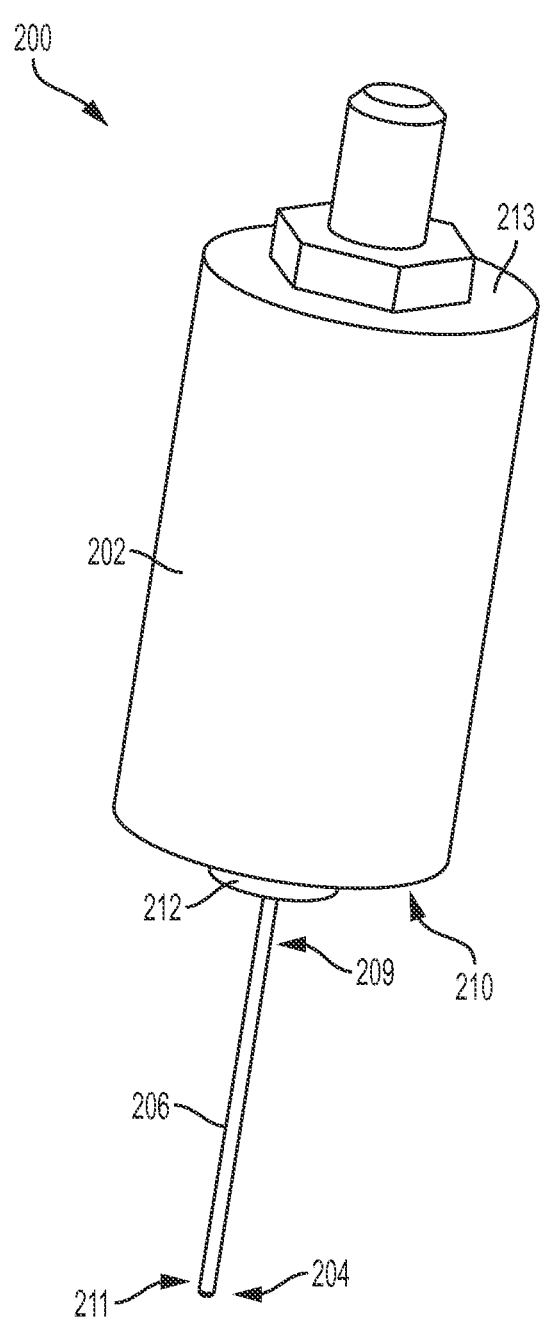
FIG. 3 shows an isometric view of a treatment apparatus, according to at least one embodiment of the present invention, having a single nozzle configuration.
Figure 4:
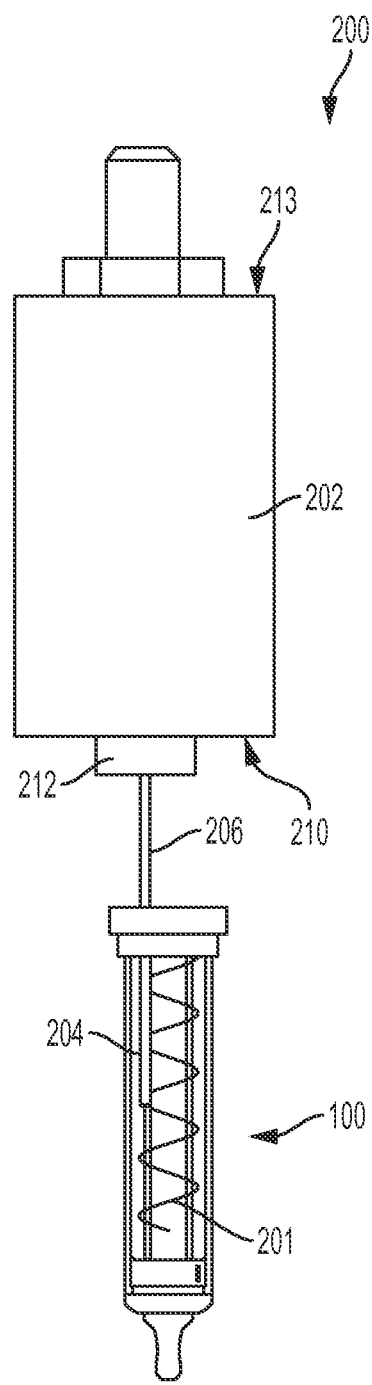
FIG. 4 shows a front view of the treatment apparatus of FIG. 3, engaged with a mixing device.

FIGS. 3-4 show an embodiment of a treatment apparatus 200 having a single nozzle 204 configured to apply a treatment, such as by applying silicone or a lubricant, to a dual concentric barrel mixing device 100. The embodiment shown in FIG. 3 is configured to apply the treatment in a diving motion, i.e., the nozzle enters the chambers of the mixing device 100 to apply the treatment, or fixed position configuration, i.e., the nozzle 204 does not translate within the mixing device by motion of the nozzle or by motion of the mixing device. In one such diving motion configuration, the nozzle 204 may be held in position and the mixing device 100 may be rotated and translated to ensure that the desired treatment of the mixing device has been performed. In another diving motion configuration, the mixing device 100 may be held in position and the nozzle 204 and/or the entire treatment apparatus 200 may be rotated and translated to ensure that the desired treatment of the mixing device has been performed. The helical line 201 is shown in FIG. 4 to convey the rotational and translational movement in either of these diving treatment embodiments. In the fixed position configuration, the spray angle of the nozzle 204 may be adjustable to reach the desired surfaces of the mixing device 100 for treatment. Accordingly, the treatment apparatus 200 may suitably treat the desired surfaces of the mixing device 100 without the need to move the nozzle 204. In either configuration, the treatment apparatus 200 includes a manifold 202 having an input end 213 and an output end 210, a header 212, a fluid conduit body 206 including a manifold end 209 and a nozzle end 211, and a nozzle 204 disposed at the nozzle end of the fluid conduit body, and is configured to treat a mixing device 100. The manifold 202 is configured to receive at least one type of fluid through the input end 213 and to convey the fluids through the header 212 and into a fluid conduit within the fluid conduit body 206. In some embodiments, the manifold 202 can include an integrated heating orifice configured to receive a heating device to regulate the temperature of incoming fluid to the manifold. The header 212 is connected to the output end 210 of the manifold 202, and the fluid conduit body 206 is connected to the header. A fluid pathway is formed between the input end 213 of the manifold 202, through the manifold to the output end 210, through the header 212, through the fluid conduit in the fluid conduit body 206, and out through the nozzle 204 at a distal end of the conduit body. In some embodiments, the manifold 202 is configured to receive at least two different types of fluid into the input end 213 that can mix upon expulsion from the nozzle 204. In some embodiments, the two fluids are air and silicone oil, though other suitable fluids are contemplated in other embodiments.

Figure 5B:
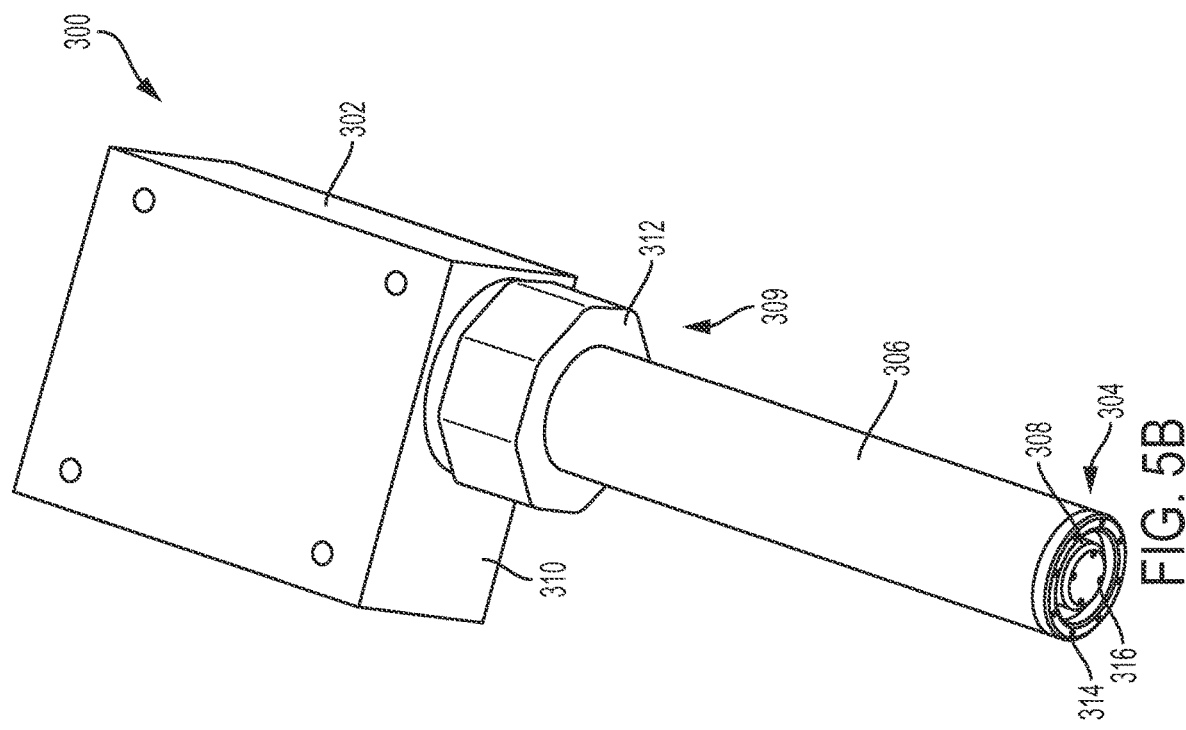
FIG. 5B shows another isometric view of the treatment apparatus of FIG. 5A.
Figure 5A:
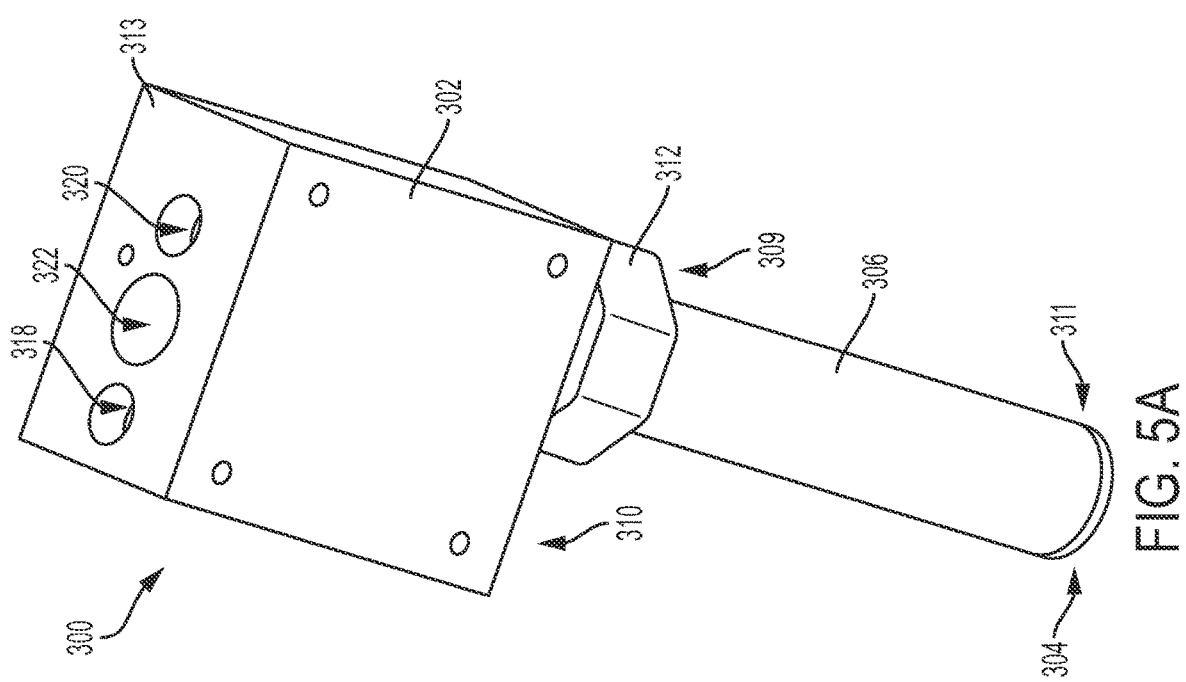
FIG. 5A shows an isometric view of a treatment apparatus, according to another embodiment of the present invention, having a multi-nozzle configuration.
Figure 6:
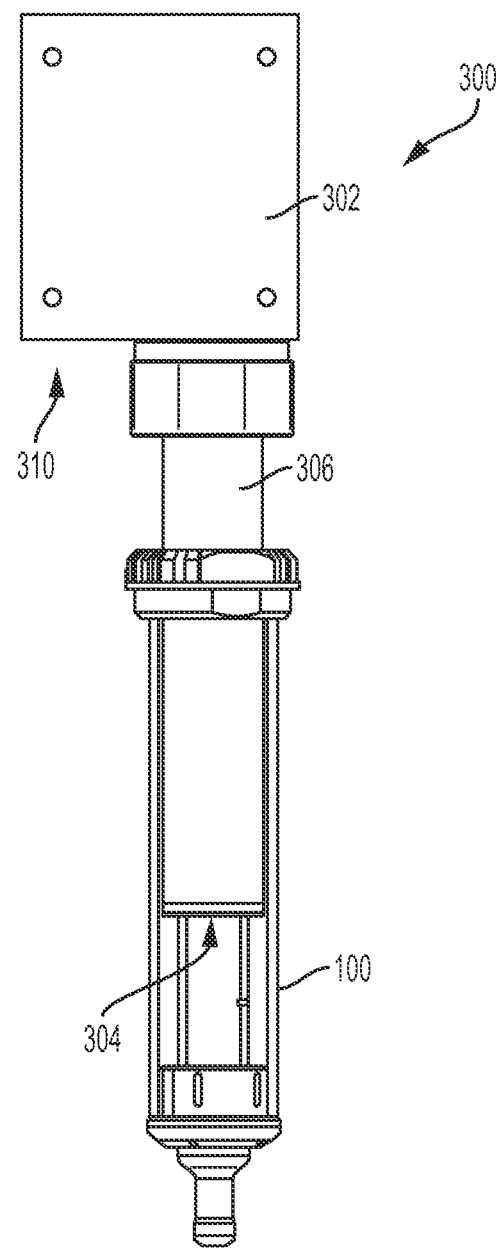
FIG. 6 shows a front view of the treatment apparatus of FIG. 5A, engaged with a mixing device.

FIGS. 5A and 5B show a treatment apparatus 300 having a multi-nozzle configuration, according to another embodiment of the present invention. FIG. 6 shows the multi-nozzle treatment apparatus 300 of FIGS. 5A and 5B engaged with a mixing device 100. As with the treatment apparatus 200 described with reference to FIGS. 3-4, the multi-nozzle treatment apparatus 300 may be held in position and the mixing device 100 may be rotated and translated to ensure that the desired treatment of the mixing device has been performed, or the mixing device 100 may be held in position and a multi-nozzle component 304 and/or entire treatment apparatus 300 may be rotated and translated to ensure that the desired treatment of the mixing device has been performed. Alternatively, the treatment apparatus 300 and multi-nozzle 304 may be configured to be in a fixed position, i.e., the multi-nozzle does not translate within the mixing device by motion of the multi-nozzle or by motion of the mixing device. In such a configuration, the spray angle of each of the nozzles of the multi-nozzle component 304 may be adjustable to reach the desired surfaces of the mixing device for treatment. Accordingly, the treatment apparatus 302 may suitably treat the desired surfaces of the mixing device 100 without the need to move the multi-nozzle component 304. In any of these embodiments, each of the nozzles of the multi-nozzle component 304 may have the same or different spray angles, as may be necessary to reach the desired treatment of the mixing device 100. A separate nozzle may exist to treat the inner chamber 112 of the mixing device 100, while the multi-nozzle component 304 is utilized to treat the outer chamber 140 of the mixing device shown in FIG. 2.

Figure 8A:
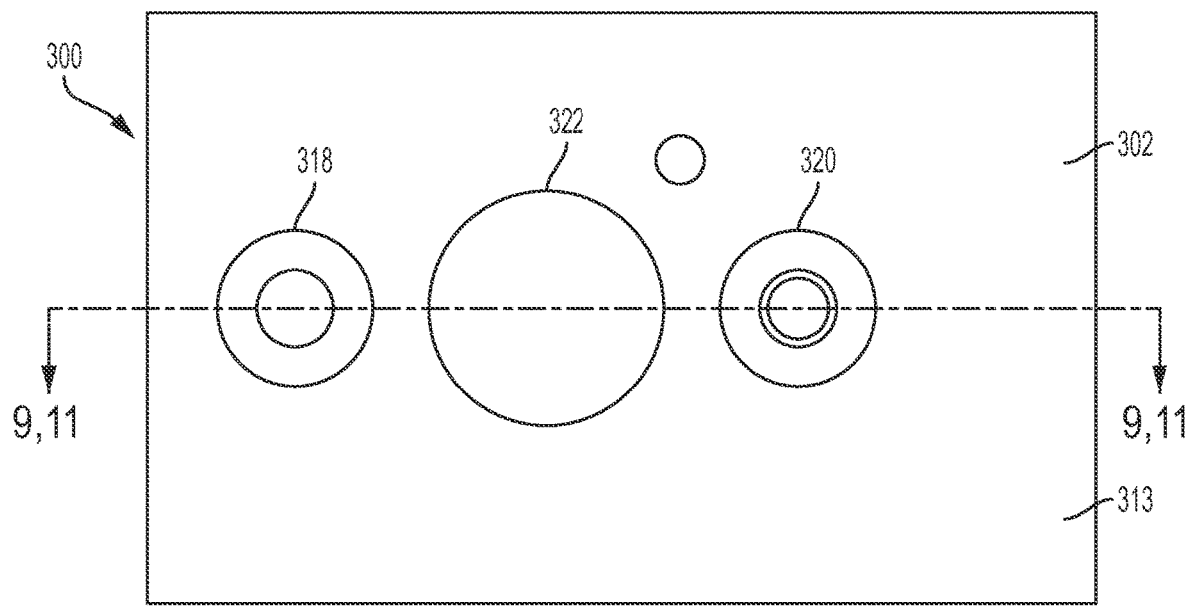
FIG. 8A shows a top view of the treatment apparatus having a multi-nozzle configuration of FIG. 5A.
Figure 8B:
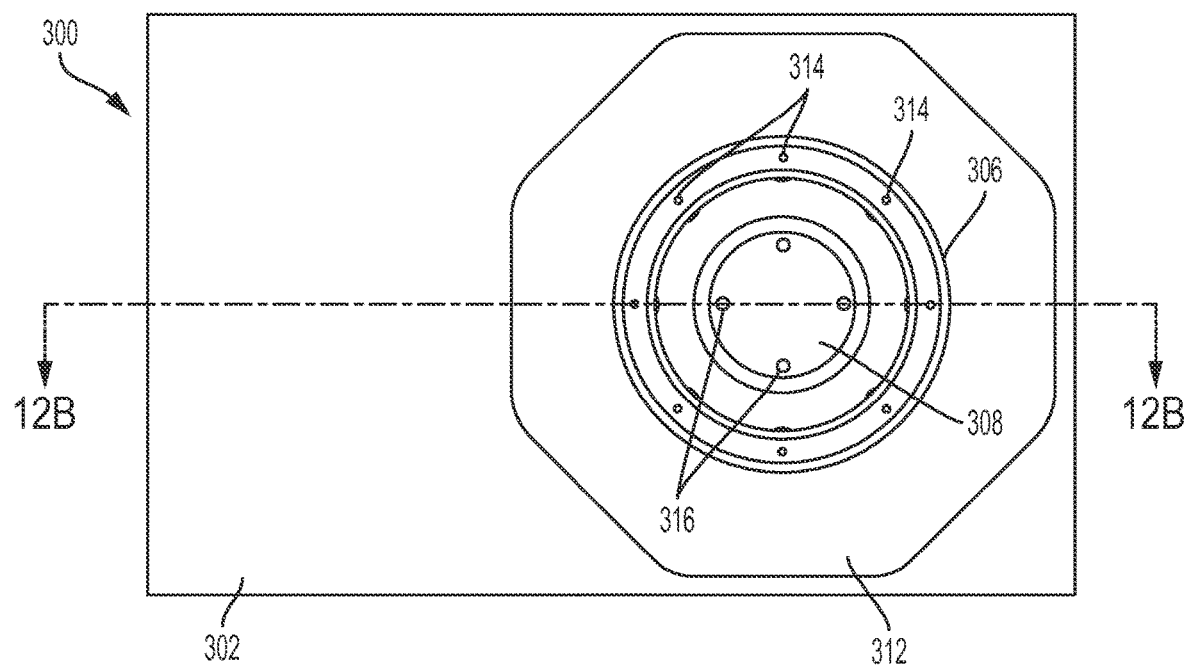
FIG. 8B shows a bottom view of the treatment apparatus having multi-nozzle configuration of FIG. 5A.

Referring again to FIGS. 5A and 5B in more detail, the treatment apparatus 300 includes a manifold 302, a multi-nozzle 304, an outer conduit body 306, and an inner conduit body 308. Manifold ends 309, 317 (see FIG. 10) of the outer and inner conduit bodies 306, 308 are connected to an output end 310 of the manifold 302 via a header 312 so as to provide fluid communication between the manifold and the nozzle component 304 at nozzle ends 311, 319 of the conduit bodies. The conduits provided in the outer and inner conduit bodies 306, 308 in order to make this fluid communication will be described below in further detail. As shown in FIG. 5B, the outer conduit body 306 includes a plurality of outer nozzles 314, and the inner conduit body 308 includes a plurality of inner nozzles 316. FIG. 8B shows a bottom view of the treatment apparatus 300 and shows another view of the outer and inner nozzles 314, 316 formed in the respective outer and inner conduit bodies 306, 308. It should be understood that, although the illustrated embodiment shows eight outer nozzles 314 and four inner nozzles 316, different numbers of inner and outer nozzles are contemplated in other embodiments.

Figure 7A:
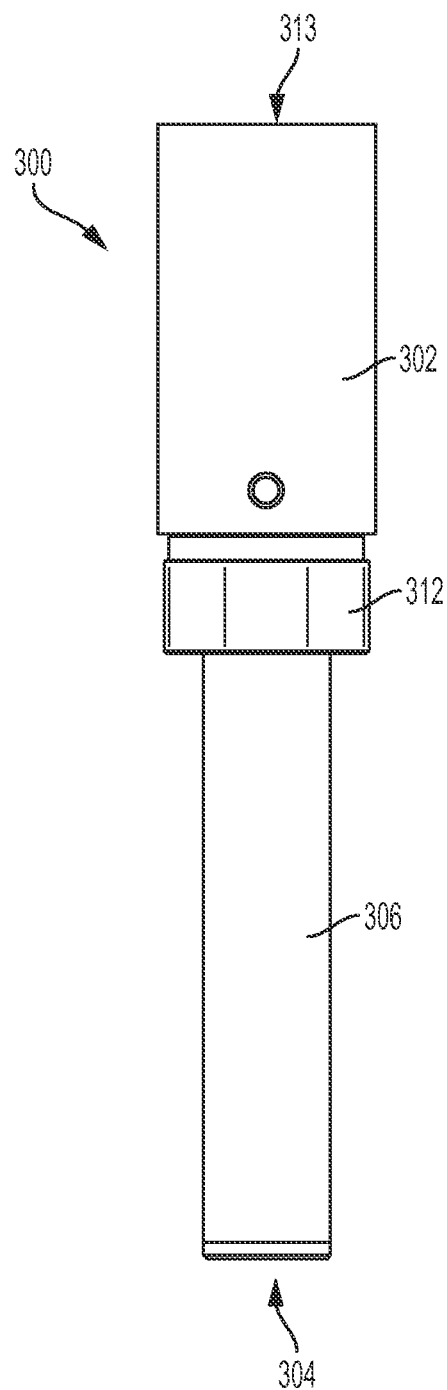
FIG. 7A shows a side view of the treatment apparatus of FIG. 5A.
Figure 7B:
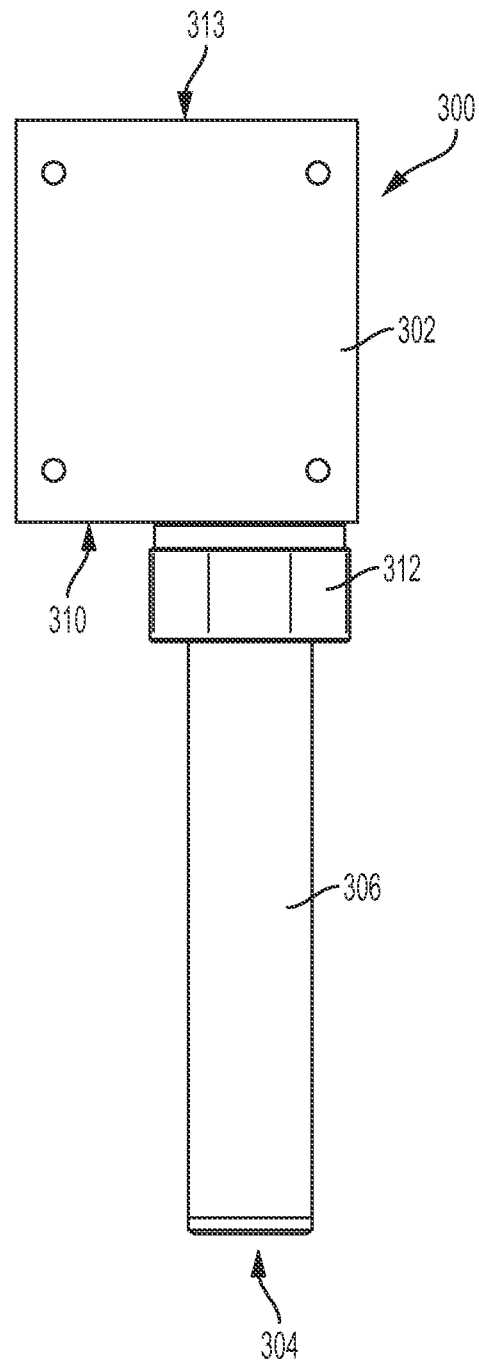
FIG. 7B shows a front view of the treatment apparatus of FIG. 5A.

Referring again to FIG. 5A, a plurality of bores can be formed into an input end 313 of the manifold 302. For example, the embodiment of the treatment apparatus 300 shown in FIG. 5A includes a first fluid bore 318, second fluid bore 320, and a heating orifice 322. The first and second fluid bores 318, 320 provide inlets into the input end 313 of the manifold 302 for various fluids, such as compressed air and/or lubricants like silicone oil, to enter the manifold. The paths of the first and second fluid bores 318, and 320 will be discussed in greater detail below. The heating orifice 322 extends at least partially into the manifold 302, and is configured to hold a heating device, such as a heating rod, to control the temperature of incoming fluid in some embodiments. The first and second bores 318, 320 and the heating orifice 322 are also shown in the top view of the treatment apparatus 300 in FIG. 8A. Additionally, FIG. 7A shows a left side view of the treatment apparatus 300, and FIG. 7B shows a front side view of the treatment apparatus 300.

Figure 9:
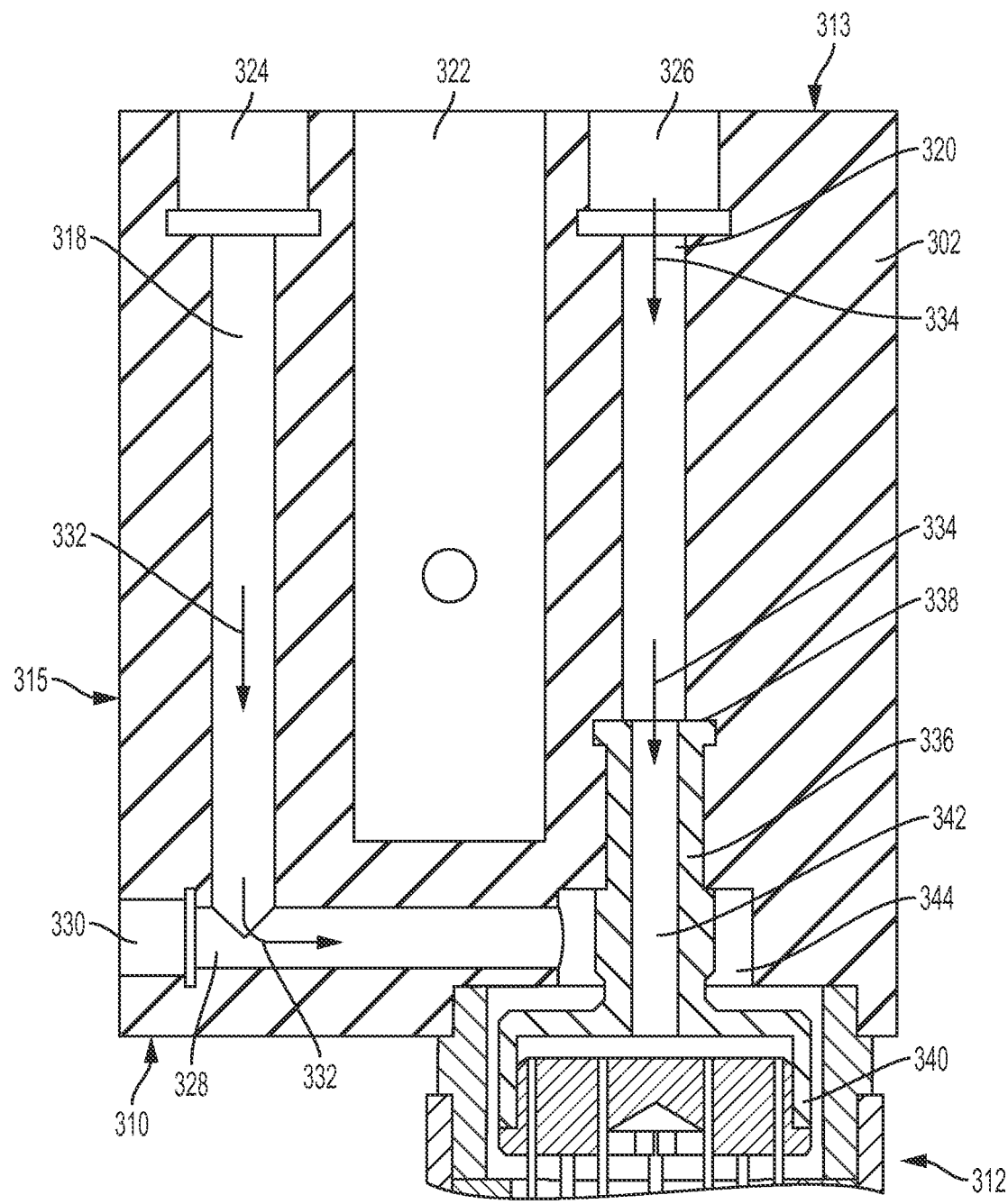
FIG. 9 shows an enlarged, front sectional view of a portion of the multi-nozzle configuration of FIG. 5A as indicated in FIG. 8A.

FIG. 9 shows a sectional view of the manifold 302 and header 312 showing a detailed view of the flow paths formed through the manifold providing fluid communication between the input end 313 and the output end 310 of the manifold. The first and second fluid bores 318, 320 each include connection adapter portions 324, 326 at the input end 313 of the manifold 302 that can accommodate input tools for providing fluids for the treatment apparatus 300 in some embodiments. A third fluid bore 328 with a third connection adapter portion 330 can also be formed into a side 315 of the manifold 302 providing a fluid pathway joining substantially perpendicularly with the first fluid bore 318. In some embodiments, the third fluid bore 328 can be plugged at the side 315 of the manifold 302 during use of the treatment apparatus 300. As shown in FIG. 9, the first fluid bore 318 is formed at least partially through the manifold 302 and fluidly communicates substantially perpendicularly with the third fluid bore 328.

The first, second, and third fluid bores 318, 320, and 328 are formed into the manifold 302 so as to provide at least two independent fluid pathways through the manifold, through header 312, and into the outer and inner conduit bodies 306, 308. The first and third fluid bores 318, 328 provide a portion of a first fluid pathway 332, while the second fluid bore 320 provides a portion of a second fluid pathway 334. In some embodiments, compressed air can flow through the first fluid pathway 332, and a lubricant or sealer, such as silicone oil, can flow through the second fluid pathway 334. It should be understood, however, that any suitable fluids can be used in either the first or second fluid pathways.

Referring again to FIG. 9, the treatment apparatus 300 includes a transition stem 336 disposed into the output end 310 of the manifold 302. The transition stem 336 has a manifold end 338 and a header end 340, with a transition bore 342 formed longitudinally through the transition stem between manifold end and the header end. The manifold end 338 is disposed within the manifold 302, while the header end 340 extends out of the manifold and into the header 312. In the illustrated embodiment, the transition stem 336 and the transition bore 342 is narrower in diameter at the manifold end 338 than the header end 340. The transition stem 336 is disposed into the output end 310 of the manifold 302 such that the fluid communication is formed between the second fluid bore 320 and the transition bore 342, providing an avenue for fluid in the second fluid pathway 334 out of the manifold 302 and into the header 312.

An output bore 344 is formed into the output end 310 of the manifold 302. The output bore 344 fluidly communicates with the third fluid bore 328 so as to provide an avenue for fluid in the first fluid pathway 332 out of the manifold 302 and into the header 312. In the illustrated embodiment, the output bore 344 is formed substantially coaxially with the second fluid bore 320; however, the transition stem 336 is disposed within the output bore 344 and into the manifold 303 such that no fluid communication exists between the second fluid bore and the output bore. The output bore 344 has a larger diameter than the transition stem 336 such that fluid in the first fluid pathway 332 can substantially surround the transition stem within the output bore and flow into the header 312.

Figure 10:
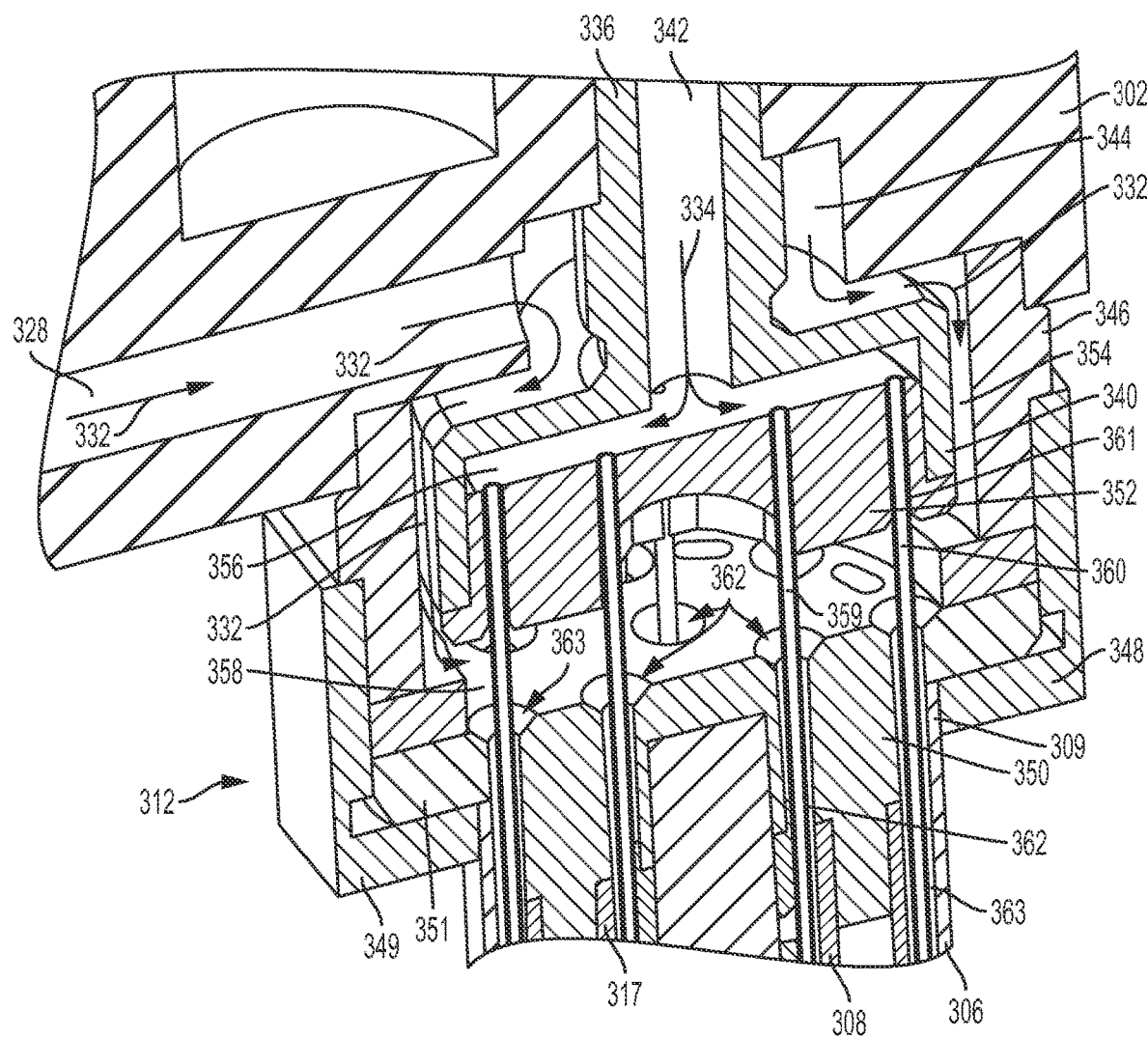
FIG. 10 shows an enlarged, isometric sectional view a portion of the multi-nozzle configuration of FIG. 5A.
Figure 11:
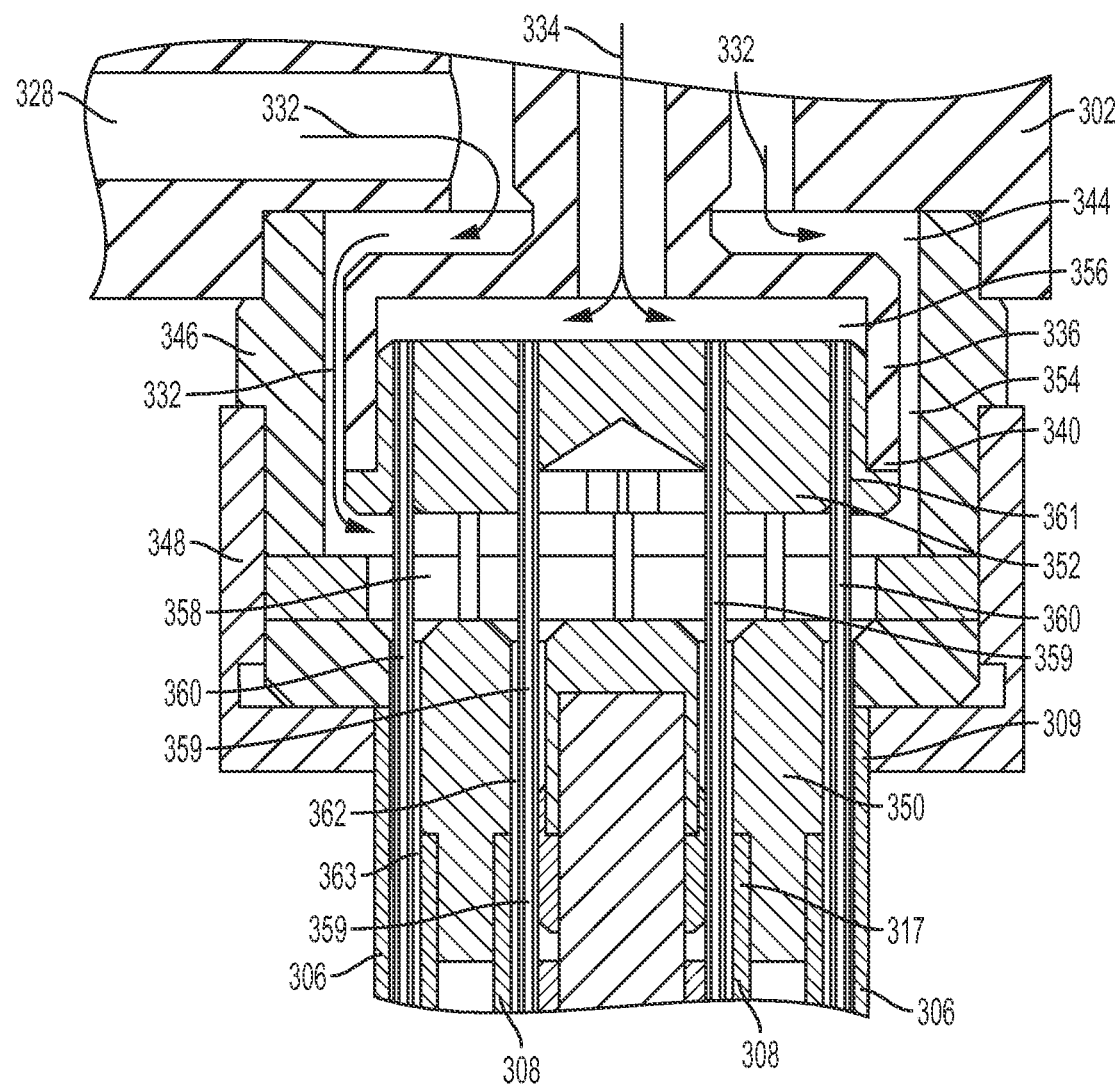
FIG. 11 shows an enlarged, front sectional view of a portion of the multi-nozzle configuration of FIG. 5A as indicated in FIG. 8A.

FIGS. 10 and 11 show an enlarged sectional view of the header 312, particularly showing how the first and second fluid pathways 332, 334 transition from the manifold 302 through the header. The header 312 includes a header collar 346, a header cap 348, a first conduit housing 350, and a second conduit housing 352. At least a portion of the header collar 346 fits into the output bore 344 on the output end 310 of the manifold 302. The header collar can be generally cylindrical in shape, forming a generally cylindrical header chamber 354 surrounding the transition stem 336 that fluidly communicates with the output bore 344. The second conduit housing 352 fits at least partially into the header end 340 of the transition stem 336 so as to define a second fluid chamber 356 between the second conduit housing and the transition stem. The second fluid chamber 356 fluidly communicates with the transition bore 342 through the transition stem. Thus, fluid in the second fluid pathway 334 can flow from the transition bore 342 into the second fluid chamber 356. The header cap 348 can fit over the header collar 346 opposite the manifold 302. A cylindrical flange portion 351 of the first conduit housing 350 abuts a lower portion 349 of the header cap 348 so as to form a first fluid chamber 358 between the first conduit housing 350 and the second conduit housing 352. The first fluid chamber 358 fluidly communicates with the header chamber 354 such that fluid in the first fluid pathway 332 can flow around the transition stem 336 and the second conduit housing 352 and into the first fluid chamber 358. Thus, fluid in the first fluid pathway 332 can flow through the manifold 302 via the first fluid bore 318 and the third fluid bore 328, into the output bore 344, around the transition stem 336, and into the first fluid chamber 358. Fluid in the second fluid pathway 334 can flow through the manifold 302 via the second fluid bore 320, through the transition stem 336 via the transition bore 342, and into the second fluid chamber 356.

Referring again to FIGS. 10 and 11, a plurality of inner fluid conduits 359 and outer fluid conduits 360 are fit into second conduit passages 361 in the second conduit housing 352. Though only two inner fluid conduits 359 and two outer fluid conduits 360 are shown in FIGS. 10 and 11, it should be understood that the second conduit housing 352 can house any number of inner and outer fluid conduits as correspond to the number of inner and outer nozzles 316, 314. The tube-shaped inner and outer fluid conduits 359, 360 provide fluid communication from the second fluid chamber 356 through the second conduit housing 252, through the first fluid chamber 358 without fluidly communicating with the first fluid chamber, and through a plurality of inner conduit passages 362 and outer conduit passages 363 in the first conduit housing 350 without fluidly communicating with the inner and outer conduit passages. Thus, the plurality of inner and outer fluid conduits 359, 360 split the second fluid pathway 334 into a plurality of second fluid pathways terminating at the inner and outer nozzles 316, 314.

The first inner and outer conduit passages 362, 363 formed through the first conduit housing 350 surround the respective inner and outer fluid conduits 359, 360 but have diameters at least slightly larger than the diameters of the inner and outer fluid second conduits. Thus, the inner and outer conduit passages 362, 363 provide fluid communication between the first fluid chamber 358 and into the first conduit housing 350 substantially surrounding each of the inner and outer fluid conduits 359, 360 and splitting the first fluid pathway 332 into a plurality of first fluid pathways terminating at the inner and outer nozzles 316, 314. The result is that the fluid from the second fluid pathway 334 can flow through the inner and outer fluid conduits 359, 360 through the first conduit housing 350 surrounded by, but not fluidly communicating with, fluid that flows along the first fluid pathway 332 into the inner and outer conduit passages 362, 363. It is contemplated, however, that in some embodiments, the first and second fluid pathways 332, 334 could merge prior to reaching the nozzles 316, 314. In such embodiments, the inner and outer fluid conduits 359, 360 could become fluidly connected with the respective inner and outer conduit passages 362, 363 after leaving the manifold 302, but prior to reaching the nozzle ends 311, 319.

As seen in FIGS. 10 and 11, the manifold end 309 of the outer conduit body 306 connects to the first conduit housing 350 such that the outer fluid conduits 360 and outer conduit passages 363 continue out of the first conduit housing and through the outer conduit body. Similarly, the inner conduit body 308 connects to the first conduit housing 350 such that the inner fluid conduits 359 and inner conduit passages 362 continue out of the first conduit housing and through the inner conduit body.

FIGS. 12A and 12B show enlarged views of the nozzle ends 311, 319 of the respective outer and inner conduit bodies 306, 308. In some embodiments, the inner fluid conduits 359 and the inner conduit passages 362 proceed through to the nozzle end 319 of the inner conduit body 308. In other embodiments, the inner fluid conduits 359 proceed through to the inner nozzles 316, while the inner conduit body 308 includes a single, annular conduit passage 362 that encompasses all of the inner fluid conduits within the inner conduit body. The inner fluid conduits 359 and the inner conduit passages 362 can both terminate at the inner nozzles 316 such that the fluid from the first fluid path 332 and the fluid from the second fluid path 334 can mix upon expulsion from the inner nozzles. Similarly, in some embodiments, the outer fluid conduits 360 and the outer conduit passages 363 proceed through to the nozzle end 311 of the outer conduit body 306. In other embodiments, the outer fluid conduits 360 proceed through to the outer nozzles 314, while the outer conduit body 306 includes a single, annular conduit passage 363 that encompasses all of the outer fluid conduits within the outer conduit body. The outer fluid conduits 360 and the outer conduit passages 363 both terminate at the outer nozzles 314 such that the fluid from the first fluid path 332 and the second fluid path 334 can mix upon expulsion from the outer nozzles. The diameter of the outer and inner nozzles 316, 314 may be as large as the conduit passages 363, 362 respectively, or substantially smaller than inner and outer fluid conduits 360, 359 respectively, or anywhere within that range. The geometry of inner and outer nozzles 316, 314 may be straight bored, chamfered, or otherwise profiled to achieve desired spray angle, shape, and other mixed fluid properties (such as droplet size of lubricant such as silicone when mixed with air).

As shown in FIG. 12B, biasing members 380 may be at least partially disposed within inner conduit passages 362 and outer conduit passages 363. They may also be at least partially disposed within nozzle ends 311, 319. The biasing members may be coil springs such as compression or tension springs. Biasing members 380 may ensure that the fluid conduits 359, 360 remain substantially centered with respect to conduit passages 362, 363 and/or nozzle ends 311, 319. Alternatively, or in addition, a sleeve such as a polymeric or metal sleeve may be disposed within the fluid conduits and/or nozzle ends to substantially center the fluid conduits therein. A centering plate at the nozzle end may also be used.

In the embodiment of the treatment apparatus 300 illustrated in FIGS. 5-12, an annular recess 366 is formed between the annular outer conduit body 306 and the annular inner conduit body 308. During the treatment of a mixing device, such as mixing device 100 shown in FIGS. 1A, 1B, and 2 of the present disclosure, the annular recess 366 allows for the inner conduit body 308 to fit within an inner barrel 112 of the mixing device, and for the outer conduit body 306 to fit within an outer barrel 306 simultaneously. Thus, the multi-nozzle treatment apparatus 300 can simultaneously clean and/or lubricate both the inner and outer barrels of a mixing device. In one embodiment of preparing such a mixing device with treatment apparatus 300, compressed air is provided into the first fluid bore 318 to flow along the first fluid pathway 332 and silicone oil is provided into the second fluid bore 320 to flow along the second fluid pathway 334. A mixture of air and silicone oil is then expelled into both the inner and outer barrels of the mixing device in order to coat the inner and outer barrels as desired for preparation of the mixing device. In some embodiments, upon exiting the nozzles 314, 316, the silicone oil is atomized, i.e., the air can shear the silicone oil, causing the oil to form droplets and thereby evenly coat the inner and outer barrels. The characteristics of the coating performed can be controlled by the pressure and temperature of the air and of the silicone oil. Additionally, it is contemplated that, in some embodiments, flow may only occur through the outer conduit housing 306 and not through the inner conduit housing 308. In such embodiments, the treatment apparatus 300 only coats the outer barrel of the mixing device 100. The inner barrel could be coated by other mechanisms, such as with the treatment device 200 described above.

Figure 19:
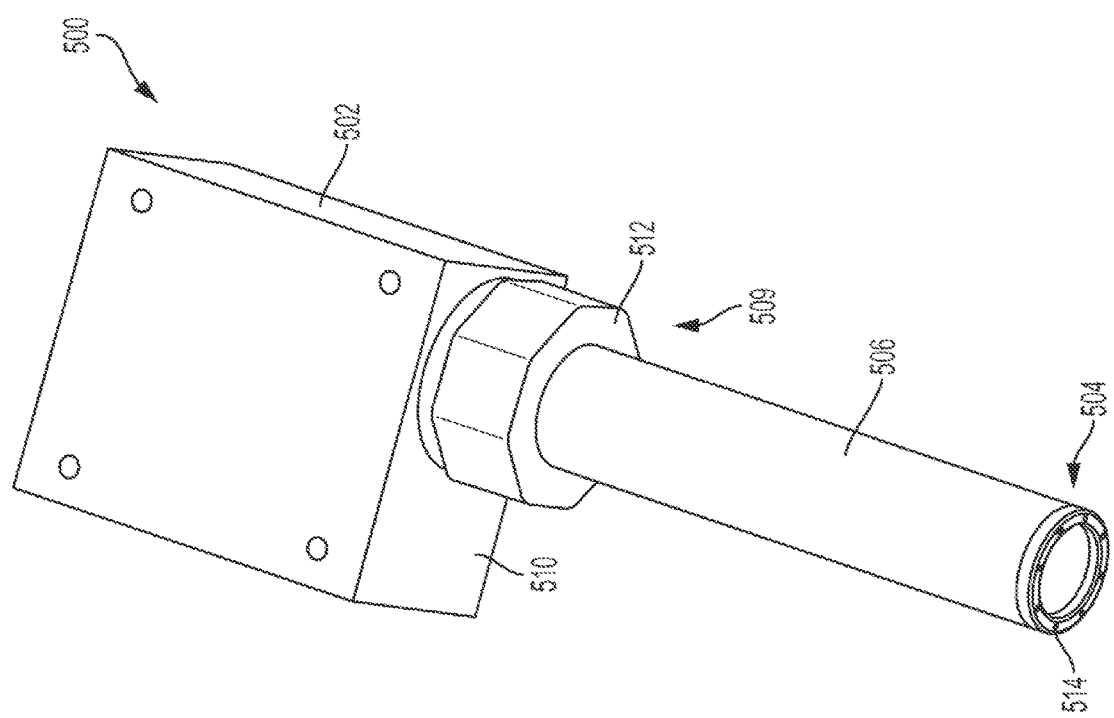
FIG. 19 is an isometric view of another embodiment of a treatment apparatus according to teachings of the present invention.

In other embodiments, shown in FIG. 19, the treatment apparatus 500 is configured to coat only the outer chamber with a fluid such as silicone oil. The treatment apparatus 500 includes a manifold 502, a multi-nozzle 504, and an outer conduit body 506. A manifold end 509 of the outer conduit body 506 is connected to an output end 510 of the manifold 502 via a header 512 so as to provide fluid communication between the manifold and the nozzle component 504 and a plurality of outer nozzles 514 at a nozzle end of the conduit body. Because the treatment apparatus 500 in FIG. 19 is configured to coat only the outer chamber of a mixing device with fluid, that embodiment of the treatment apparatus need not include an inner conduit body or corresponding inner nozzles, inner fluid conduits, or inner conduit passages. Unless otherwise noted, however, it should be understood that the treatment apparatus 500 shown in FIG. 19 includes substantially similar features as those described with respect to the treatment apparatus 300 described herein. Additionally, in some embodiments, a solid inner core may be used in place of inner nozzles and, during use, enter the inner barrel mixing device. Prior to, concurrently, or after treatment of the outer chamber of the mixing device with such a treatment apparatus a traditional siliconization nozzle may be used to treat the inner chamber.

Some embodiments may include a plurality of treatment apparatuses 300 arranged so as to simultaneously clean or coat a plurality of mixing devices 100. The air and silicone (or other fluid) can be provided to the single or plurality of treatment apparatuses by filling or cleaning tools known in the art.

FIGS. 13-18 show another embodiment of a treatment apparatus 400 having multiple nozzles. As with the treatment apparatus 200 described with reference to FIGS. 3-4 and the treatment apparatus 300 described with reference to FIGS. 5-12, the multi-nozzle treatment apparatus 400 may be held in position and the mixing device 100 may be rotated and translated to ensure that the desired treatment of the mixing device has been performed, or the mixing device 100 may be held in position and a multi-nozzle component 404 and/or entire treatment apparatus 400 may be rotated and translated to ensure that the desired treatment of the mixing device has been performed. Alternatively, the treatment apparatus 400 and multi-nozzle 404 may be configured to be in a fixed position, i.e., the multi-nozzle does not translate within the mixing device by motion of the multi-nozzle or by motion of the mixing device. In such a configuration, the spray angle of each of the nozzles of the multi-nozzle component 404 may be adjustable to reach the desired surfaces of the mixing device for treatment. Accordingly, the treatment apparatus 402 may suitably treat the desired surfaces of the mixing device 100 without the need to move the multi-nozzle component 404. In any of these embodiments, each of the nozzles of the multi-nozzle component 404 may have the same or different spray angles, as may be necessary to reach the desired treatment of the mixing device 100. A separate nozzle may exist to treat the inner chamber of the mixing device 100, while the multi-nozzle component 404 is utilized to treat the outer chamber of the mixing device.

Figure 15B:
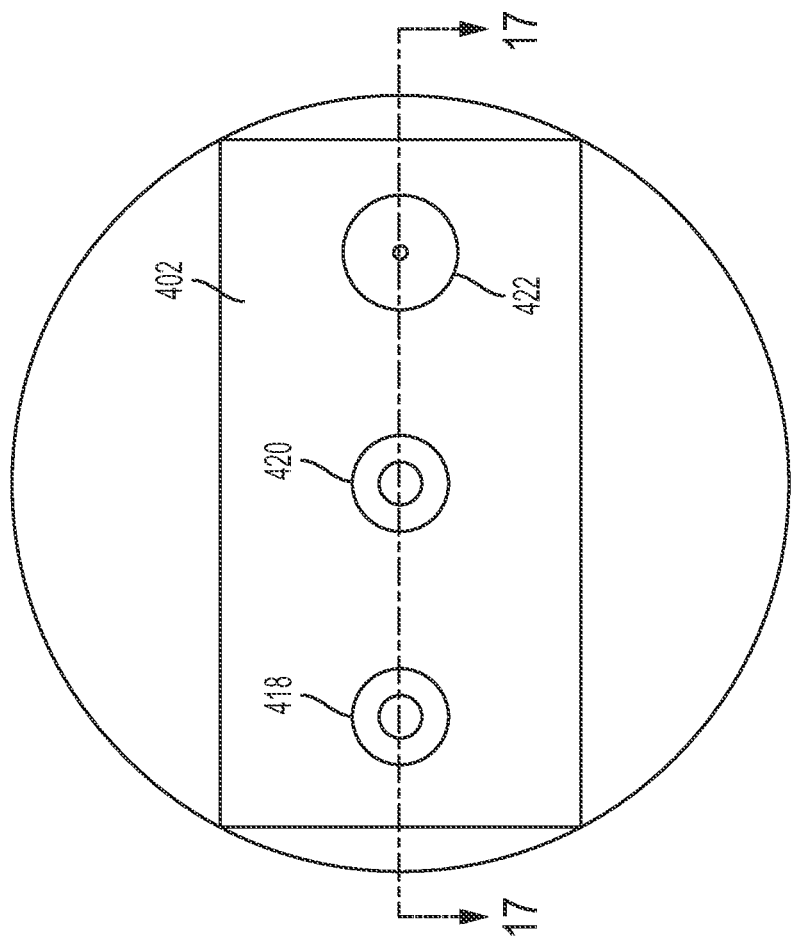
FIG. 15B shows a top view of the treatment apparatus of FIG. 13A.
Figure 15A:
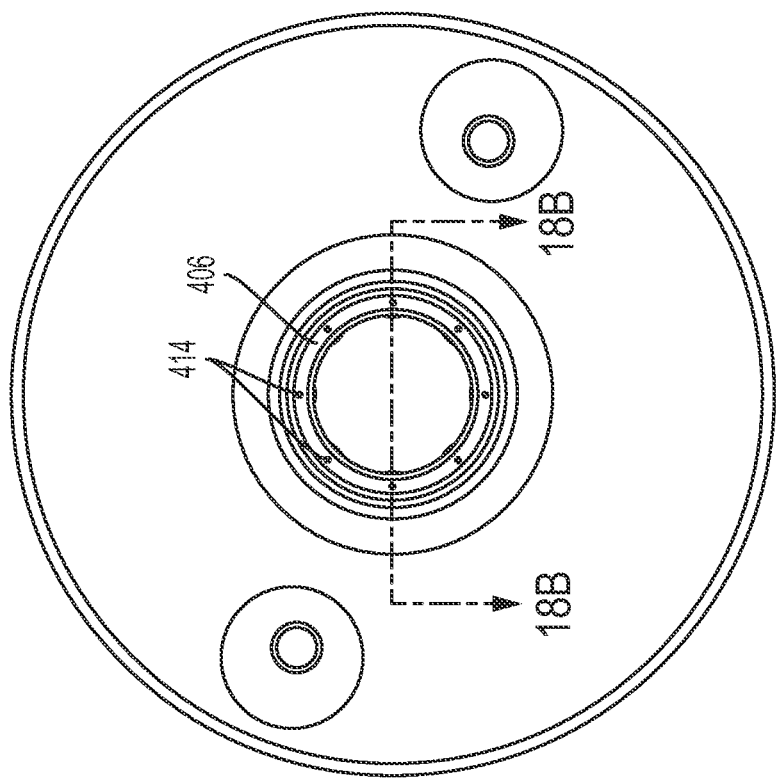
FIG. 15A shows a bottom view of the treatment apparatus of FIG. 13A.

Referring to FIGS. 13A and 13B, the treatment apparatus 400 the includes a manifold 402, a multi-nozzle 404, and an annular outer conduit body 406. A manifold end 409 of the outer conduit body 406 is connected to an output end 410 of the manifold 402 via a header 412 so as to provide fluid communication between the manifold and the nozzle component 404 at a nozzle end 411 of the conduit body. The conduits provided in the outer conduit body 406 in order to make this fluid communication will be described below in further detail. As shown in FIG. 13B, the outer conduit body 406 includes a plurality of outer nozzles 414. FIG. 15A shows a bottom view of the treatment apparatus 400 and shows another view of the outer nozzles 414 formed in the outer conduit body 406. It should be understood that, although the illustrated embodiment shows eight outer nozzles 414, different numbers of outer nozzles are contemplated in other embodiments.

Referring again to FIG. 13A, a plurality of bores can be formed into an input end 413 of the manifold 402. For example, the embodiment of the treatment apparatus 400 shown in FIG. 13A includes a first fluid bore 418, second fluid bore 420, and a heating orifice 422. The first and second fluid bores 418, 420 provide inlets into the input end 413 of the manifold 402 for various fluids, such as compressed air and/or lubricants like silicone oil, to enter the manifold. The paths of the first and second fluid bores 418, and 420 will be discussed in greater detail below. The heating orifice 422 extends at least partially into the manifold 402, and is configured to hold a heating device, such as a heating rod, to control the temperature of incoming fluid in some embodiments. The first and second bores 418, 420 and the heating orifice 422 are also shown in the top view of the treatment apparatus 400 in FIG. 15B. Additionally, FIG.

Figure 14A:
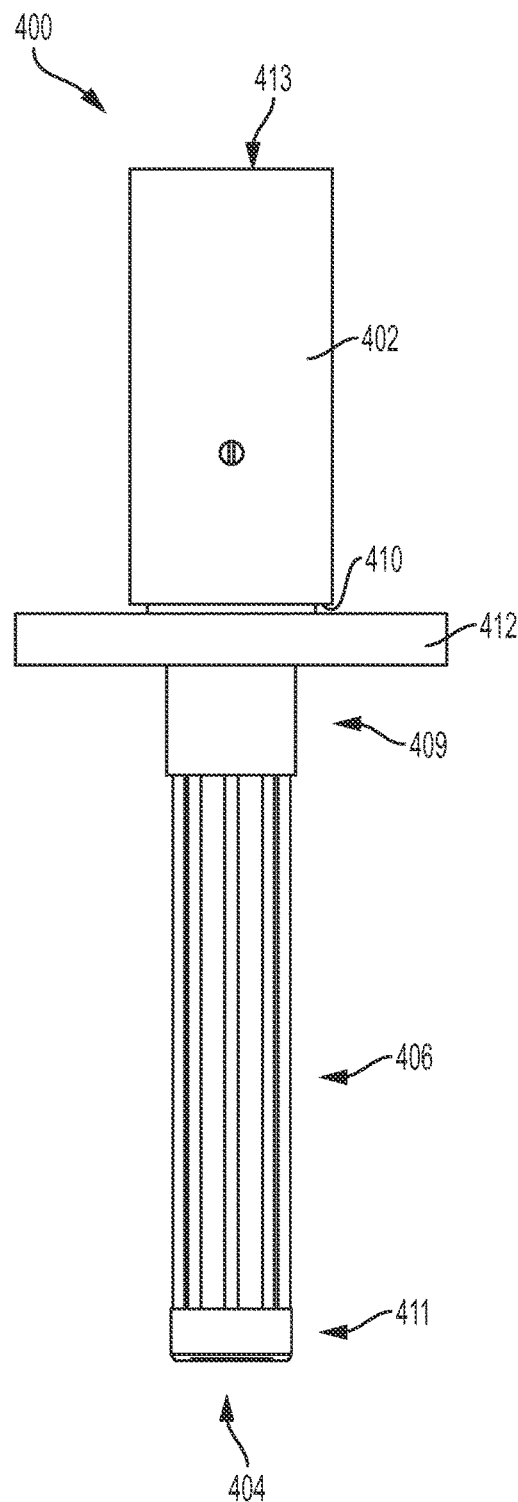
FIG. 14A shows a right side view of the treatment apparatus of FIG. 13A.
Figure 14B:
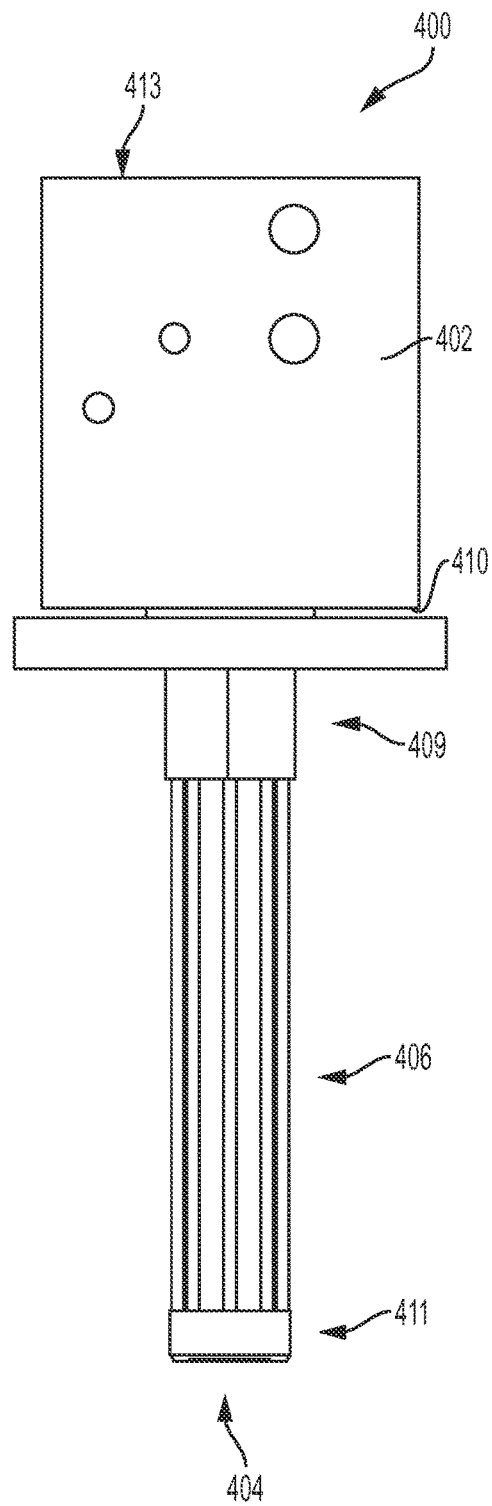
FIG. 14B shows a front view of the treatment apparatus of FIG. 13A.

14A shows a left side view of the treatment apparatus 400, and FIG. 14B shows a front side view of the treatment apparatus 400.

Figure 16:
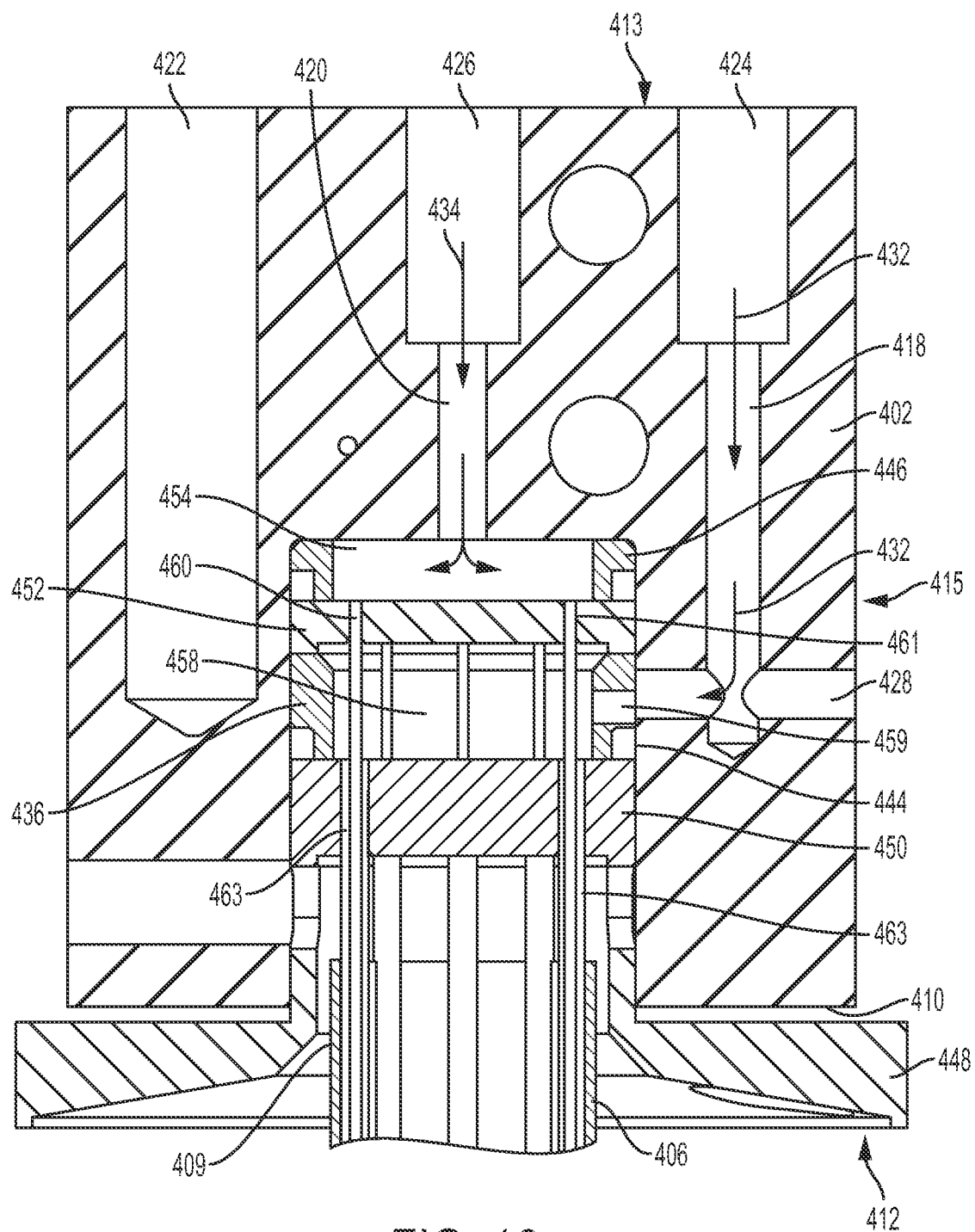
FIG. 16 shows an enlarged, isometric sectional view of a portion of the treatment apparatus of FIG. 13A.

FIG. 16 shows a sectional view of the manifold 402 and header 412 showing a detailed view of the flow paths formed through the manifold providing fluid communication between the input end 413 and the output end 410 of the manifold. The first and second fluid bores 418, 420 each include connection adapter portions 424, 426 at the input end 413 of the manifold 402 that can accommodate input tools for providing fluids for the treatment apparatus 400 in some embodiments. A third fluid bore 428 can also be formed into a side 415 of the manifold 402 providing a fluid pathway joining substantially perpendicularly with the first fluid bore 418. In some embodiments, the third fluid bore 428 can be plugged at the side 415 of the manifold 402 during use of the treatment apparatus 400. As shown in FIG. 16, the first fluid bore 418 is formed at least partially through the manifold 402 and fluidly communicates substantially perpendicularly with the third fluid bore 428.

The first, second, and third fluid bores 418, 420, and 428 are formed into the manifold 402 so as to provide at least two independent fluid pathways through the manifold, through header 412, and into the outer conduit body 406. The first and third fluid bores 418, 428 provide a first fluid pathway 432, while the second fluid bore 420 provides a second fluid pathway 434. In some embodiments, compressed air can flow along the first fluid pathway 432, and a lubricant, such a silicone oil, can flow along the second fluid pathway 434. It should be understood, however, that any suitable fluids can be used in either the first or second fluid pathways.

Figure 17:
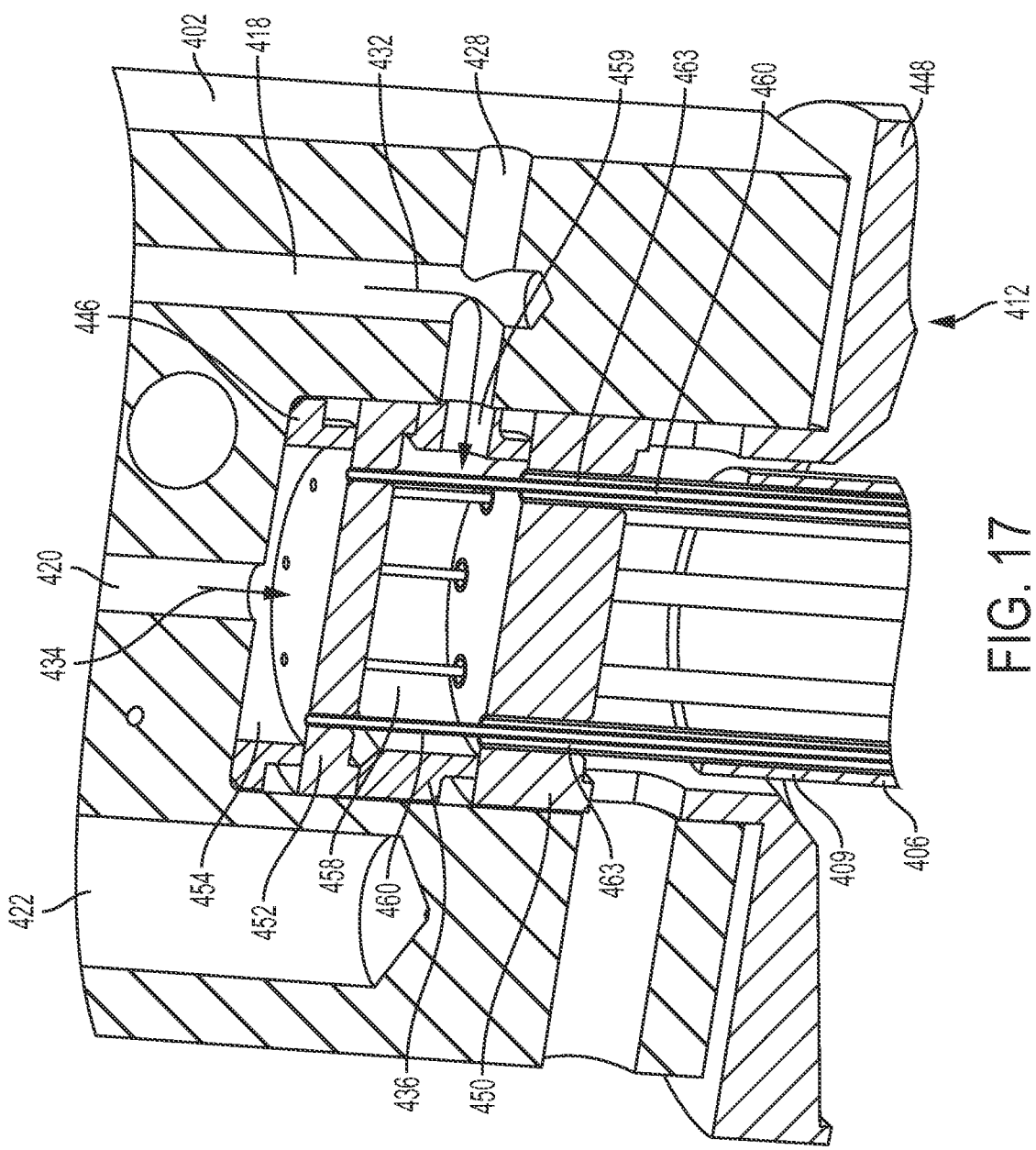
FIG. 17 shows an enlarged, front sectional view of a portion of the treatment apparatus of FIG. 13A.

FIGS. 16 and 17 show enlarged sectional views of the header 412, particularly showing how the first and second fluid pathways 432, 434 transition from the manifold 402 through the header. The manifold 402 includes an output bore 444 in which the header 412 is disposed. The header 412 includes a first header collar 436, a second header collar 446, a first conduit housing 450, a second conduit housing 452, and a housing cap 448. The first and second header collars 436, 446 as well as the first and second conduit housings 450, 452 are disposed within the output bore 444. The housing cap 448 is disposed at least partially into the output bore 444.

The second header collar 446 can be generally cylindrical in shape, forming a generally cylindrical second header chamber 454 that fluidly communicates with the second fluid bore 420. Thus, fluid flowing along the second fluid pathway 434 can flow from the second fluid bore 420 in the manifold 402 into the second header chamber 454. The second conduit housing 452 is disposed within the output bore 444 abutting against the second header collar 446 and enclosing the second header chamber 454. The first header collar 436 is disposed within the output bore 444 so as to abut the second conduit housing 452. The first header collar 436 is substantially annular and forms a cylindrical first header chamber 458. A collar passage 459 is formed through the wall of the first header collar 436 that forms a fluid connection between the third fluid bore 428 and the first header chamber 458. Thus, fluid in the first fluid pathway 432 can flow through the manifold 402 via the first fluid bore 418 and the third fluid bore 428, through the collar passage 459 and into the first header chamber 458.

Referring again to FIGS. 16 and 17, a plurality of outer fluid conduits 460 are fit into conduit passages 461 in the second conduit housing 452. Though only two outer fluid conduits 460 are shown in FIGS. 16 and 17, it should be understood that the second conduit housing 452 can house any number of outer fluid conduits as correspond to the number of outer nozzles 414. The tube-shaped outer fluid conduits 460 provide fluid communication from the second header chamber 454 through the second conduit housing 452, through the first header chamber 458 without fluidly communicating with the first fluid chamber, and into a plurality of outer conduit passages 463 in the first conduit housing 450 without fluidly communicating with the outer conduit passages. Thus, the plurality of outer fluid conduits 460 split the second fluid pathway 434 into a plurality of second fluid pathways terminating at the outer nozzles 414.

The outer conduit passages 463 formed through the first conduit housing 450 surround the respective outer fluid conduits 460 but have diameters at least slightly larger than the diameters of the outer fluid conduits. Thus, the outer conduit passages 463 provide fluid communication between the first fluid chamber 458 and into the first conduit housing 450 substantially surrounding each of the outer fluid conduits 460 and splitting the first fluid pathway 432 into a plurality of first fluid pathways terminating at the outer nozzles 414. The result is that the fluid from the second fluid pathway 434 can flow through the outer fluid conduits 460 through the first conduit housing 450 surrounded by, but not fluidly communicating with, fluid that flows along the first fluid pathway 432 into the outer conduit passages 463.

As seen in FIGS. 16 and 17, the manifold end 409 of the outer conduit body 406 connects to header 412 such that the outer fluid conduits 460 and outer conduit passages 463 continue out of the first conduit housing and through the outer conduit body. FIGS. 12A and 12B show enlarged views of the nozzle ends 419 of the outer conduit body 406. The outer fluid conduits 460 and the outer conduit passages 463 proceed through to the nozzle end 411 of the outer conduit body 406. The outer fluid conduits 460 and the outer conduit passages 463 both terminate at the outer nozzles 414 such that the fluid from the first fluid path 432 and the second fluid path 434 can mix upon expulsion from the outer nozzles. It is contemplated, however, that in some embodiments, the first and second fluid pathways 432, 434 could merge prior to reaching the nozzles 414. In such embodiments, the outer fluid conduits 460 and outer conduit passages 463 could become fluidly connected after leaving the manifold 402, but prior to reaching the nozzle ends 411. The diameter of the outer nozzles 414 may be as large as the conduit passages 463 respectively, or substantially smaller than outer fluid conduits 360 respectively, or anywhere within that range. The geometry of outer nozzles 314 may be straight bored, chamfered, or otherwise profiled to achieve desired spray angle, shape, and other mixed fluid properties (such as droplet size of lubricant such as silicone when mixed with air).

FIGS. 18A and 18B show enlarged views of the nozzle end 411 of the outer conduit body 406. The outer fluid conduits 460 and the outer conduit passages 463 proceed through to the nozzle end 411 of the outer conduit body 406. The outer fluid conduits 460 and the outer conduit passages 463 both terminate at the outer nozzles 414 such that the fluid from the first fluid path 432 and the second fluid path 434 can mix upon expulsion from the outer nozzles. As shown in FIG. 18B, spacers 480 may be at least partially disposed within outer conduit passages 463 and be disposed about outer fluid conduits 460. Spacers 480 may ensure that fluid conduits 460 remain substantially concentric with conduit passages 463 and there may be any number of spacers disposed along the length of the fluid conduits.

Spacers 480 may be porous or contain passages therethrough, thereby allowing the passage of fluid through outer conduit passages 463.

In the embodiment of the treatment apparatus 400 illustrated in FIGS. 13-18, a annular recess 466 is formed within the annular outer conduit body 406. During the treatment of a mixing device, such as mixing device 100 shown in FIGS. 1A, 1B, and 2 of the present disclosure, the annular recess 466 allows for the outer conduit body 406 to fit within an outer barrel 140 of the mixing device, for example, to lubricate surfaces of the outer chamber 140 shown in FIG. 2. Thus, the multi-nozzle treatment apparatus 400 can clean and/or lubricate an inner surface of the outer barrel 140 and, optionally, the outer surface of inner barrel 110 of the mixing device. In one embodiment of cleaning and/or coating such a mixing device with treatment apparatus 400, compressed air is provided into the first fluid bore 418 to flow along the first fluid pathway 432 and silicone oil is provided into the second fluid bore 420 to flow along the second fluid pathway 434. A mixture of air and silicone oil is then expelled into the outer barrels of the mixing device in order to coat the outer barrel as desired for preparation of the mixing device. In some embodiments, upon exiting the nozzles 414, the air can shear the silicone oil, causing the oil to form droplets and thereby evenly coat the outer barrels. The characteristics of the coating performed can be controlled by the pressure and temperature of the air and of the silicone oil. In such embodiments, the treatment apparatus 400 may only coat the outer barrel of the mixing device 100. The inner barrel could be coated by other mechanisms, such as with the treatment device 200 described above.

In yet another embodiment, the mixing device may be treated by a system that includes one or more of: washing, masking, treating, and assembling, such as by glue or adhesive, the components of the mixing device. For example, the outer barrel of the mixing device may be treated by one or more of the treatment systems and methodologies explained above, such that the interior of the outer barrel is treated with a silicone, lubricant, or other treatment. The inner surface of the inner barrel of the mixing device may be treated similarly. The outer surface of the inner barrel may also require treatment, and may be treated similarly. Additionally or alternatively, one or more barrels may be treated by utilizing other treatment methodologies. For example, a perpendicular spray nozzle configuration may be utilized to spray or treat the barrels at an angle (90 degree or otherwise) instead of axially within the barrel. The perpendicular nozzle may be rotated around the barrel and translated to provide treatment to the desired surfaces, or the nozzle may be held static in position and the barrel may be rotated/translated to provide treatment to the desired surfaces. The surfaces that do not need to be treated, or are undesired to be treated, may be masked by a tape or other material to prevent the treatment contacting the barrel. For example, the portions of the barrels that are to be connected, such as by a glue or adhesive, with or without the use of an additional component, such as a plastic barrel attachment, may be masked to prevent treatment. The masked portions may be unmasked after treatment.

Each of the treatment systems and methodologies described herein may utilize additional known apparatus, or procedural steps, that are known in the art. For example, the barrels may be washed before, during, and/or after treatment. Similarly, the barrels of the mixing device may be treated, such as by a silicone or lubricant, one or more times utilizing the present invention. Throughout the specification, the aim has been to describe the preferred embodiments of the invention without limiting the invention to any one embodiment or specific collection of features. Various changes and modifications may be made to the embodiments described and illustrated without departing from the present invention.

The disclosure of each patent and scientific document, computer program and algorithm referred to in this specification is incorporated by reference in its entirety.

We claim:

1. A treatment apparatus for a mixing device having a concentric barrel configuration, the treatment apparatus comprising:
   a manifold including an input end and an output end, a first fluid bore and a second fluid bore being formed into the input end of the manifold;
   a substantially tubular outer conduit body having a manifold end and a nozzle end, the manifold end being connected to the output end of the manifold, the outer conduit body including:
   a plurality of outer nozzles disposed in an annular pattern at the nozzle end of the outer conduit body opposite the manifold;
   a plurality of outer fluid conduits disposed within the outer conduit body, each of the outer fluid conduits being in fluid communication with both the second fluid bore and one of the plurality of outer nozzles;
   at least one outer conduit passage formed within the outer conduit body, the at least one outer conduit passage being in fluid communication with both the first fluid bore and at least one of the plurality of outer nozzles;
   wherein the first fluid bore and the at least one outer conduit passage define at least a portion of a first fluid pathway formed between the input end of the manifold and one of the plurality of outer nozzles, and the second fluid bore and each of the plurality of outer fluid conduits define at least a portion of a second fluid pathway formed between the input end of the manifold and one of the plurality of outer nozzles, the first fluid pathway and the second fluid pathway being distinct fluid pathways, the plurality of outer fluid conduits and the at least one outer conduit passage terminating at the outer nozzles disposed at the nozzle end of the outer conduit body such that mixing of fluid from the first fluid pathway and fluid from the second fluid pathway is initiated at the plurality of outer nozzles and occurs upon expulsion of the fluids from the treatment apparatus; and
   wherein a recess is formed within and coaxial with the tubular outer conduit body, the recess being configured to receive at least a portion of the mixing device, the recess comprising an opening at the nozzle end of the outer conduit body to receive the concentric barrel configuration of the mixing device, the recess comprising an opening at the nozzle end of the outer conduit body to receive the concentric barrel configuration of the mixing device.

2. The treatment apparatus of claim 1, wherein each of the plurality of outer fluid conduits is substantially tubular in shape, and the at least one outer conduit passage is formed within the outer conduit body so as to substantially surround at least one of the plurality of outer fluid conduits.

3. The treatment apparatus of claim 2, wherein the recess comprises a cylindrical recess.

4. The treatment apparatus of claim 1, further comprising a substantially cylindrical inner conduit body having a manifold end and a nozzle end, the manifold end being connected to the output end of the manifold, and the inner conduit body including:
- at least one inner nozzle at the nozzle end of the inner conduit body opposite the manifold end;
- at least one inner fluid conduit disposed within the inner conduit body, the at least one inner fluid conduit being in fluid communication with both the second fluid bore and the at least one inner nozzle; and
- at least one inner conduit passage formed within the inner conduit body, the at least one inner conduit passage being in fluid communication with both the first fluid bore and the at least one inner nozzle;
- wherein the first fluid bore and the at least one inner conduit passage define at least a portion of the first fluid pathway, and the second fluid bore and the at least one inner fluid conduit define at least a portion of the second fluid pathway.

5. The treatment apparatus of claim 4, wherein:
each of the plurality of outer fluid conduits is substantially tubular in shape, and wherein the at least one outer conduit passage is formed within the outer conduit body so as to substantially surround at least one of the outer fluid conduits; and
each of the at least one inner fluid conduits is substantially tubular in shape, and wherein each of the at least one inner conduit passage is formed within the inner conduit body so as to substantially surround the at least one inner fluid conduit.

6. The treatment apparatus of claim 5, wherein the recess comprises an annular recess formed between the outer conduit body and the inner conduit body.

7. The treatment apparatus of claim 4, wherein the recess comprises an annular recess formed between the outer conduit body and the inner conduit body.

8. A method of treating a mixing device having a concentric barrel configuration comprising an inner barrel and a concentric outer barrel, the method comprising:
providing at least one treatment apparatus, each treatment apparatus comprising:
(i) a manifold having an input end and an output end, a first fluid bore and a second fluid bore formed into the input end of the manifold;
(ii) a substantially tubular outer conduit body with a manifold end and a nozzle end, the manifold end being connected to the output end of the manifold, the outer conduit body including:
a plurality of outer nozzles disposed in an annular pattern at the nozzle end of the outer conduit body opposite the manifold end,
a plurality of outer fluid conduits disposed within the outer conduit body, each of the outer fluid conduits being in fluid communication with both the second fluid bore and one of the plurality of outer nozzles,
and at least one outer conduit passage formed within the outer conduit body, the at least one outer conduit passage being in fluid communication with both the first fluid bore and at least one of the plurality of outer nozzles;
wherein the first fluid bore and the at least one outer conduit passage define a first fluid pathway formed between the input end of the manifold and one of the plurality of outer nozzles, and wherein the second fluid bore and each of the plurality of outer fluid conduits define a second fluid pathway formed between the input end of the manifold and one of the plurality of outer nozzles, the first fluid pathway and the second fluid pathway being distinct fluid pathways, the plurality of outer fluid conduits and the at least one outer conduit passage terminating at the outer nozzles disposed at the nozzle end of the outer conduit body such that mixing of fluid from the first fluid pathway and fluid from the second fluid pathway is initiated at the plurality of outer nozzles and occurs upon expulsion of the fluids from the treatment apparatus;
wherein a recess is formed within and coaxial with the tubular outer conduit body, the recess being configured to receive at least a portion of the mixing device, the recess comprising an opening at the nozzle end of the outer conduit body to receive the concentric barrel configuration of the mixing device; the method further comprising
feeding a first fluid into the first fluid bore such that the first fluid flows along the first fluid pathway and is expelled through the at least one nozzle;
feeding a second fluid into the second fluid bore simultaneous to feeding the first fluid into the first fluid bore such that the second fluid flows along the second fluid pathway and is expelled through the at least one nozzle simultaneously with the first fluid; and
disposing the at least one nozzle within at least one of the inner barrel or the outer barrel of the mixing device.

9. The method of claim 8, wherein each of the plurality of outer fluid conduits is substantially tubular in shape, and wherein the at least one outer conduit passage is formed within the outer conduit body so as to substantially surround at least one of the plurality of outer fluid conduits.

10. The method of claim 9, wherein a cylindrical recess is formed within and coaxial with the tubular outer conduit body, the recess receiving at least a portion of the mixing device when the plurality of nozzles are disposed within at least one of the inner barrel or the outer barrel of the mixing device.

11. The method of claim 9, wherein the outer conduit body includes a plurality of fluid conduits and a plurality of corresponding nozzles disposed in an annular pattern.

12. The method of claim 11, wherein a cylindrical recess is formed within and coaxial with the tubular conduit body, the recess receiving at least a portion of the mixing device when the plurality of nozzles are disposed within at least one of the inner barrel or the outer barrel of the mixing device.

13. The method of claim 8, wherein the outer conduit body includes a plurality of fluid conduits and a plurality of corresponding nozzles disposed in an annular pattern.

14. The method of claim 13, wherein the treatment apparatus further comprises an inner conduit body with a manifold end connected to the output end of the manifold, the inner conduit body being coaxial with and surrounded by the outer conduit body, the inner conduit body including:
at least one inner nozzle at a nozzle end of the inner conduit body opposite the manifold end;
at least one inner fluid conduit providing fluid communication between the second fluid bore and the at least one inner nozzle; and
at least one inner conduit passage providing fluid communication between the first fluid bore and the at least one inner nozzle;
wherein at least a portion of the first fluid pathway is formed through the first fluid bore and the at least one inner conduit passage, and at least a portion of the second fluid pathway is formed through the second fluid bore and the at least one inner fluid conduit.

15. The method of claim 14, further comprising disposing the at least one inner nozzle within the inner barrel of the mixing device and simultaneously disposing the plurality of outer nozzles within the outer barrel of the mixing device so as to simultaneously treat both the inner and outer barrels of the mixing device.

16. The method of claim 13, wherein a cylindrical recess is formed within and coaxial with the tubular conduit body, the recess receiving at least a portion of the mixing device when the plurality of nozzles are disposed within at least one of the inner barrel or the outer barrel of the mixing device.

* * * * *